United States Patent
Hober

(10) Patent No.: US 9,534,023 B2
(45) Date of Patent: *Jan. 3, 2017

(54) MUTATED IMMUNOGLOBULIN-BINDING PROTEIN

(71) Applicant: GE Healthcare Bio-Sciences AB, Uppsala (SE)

(72) Inventor: Sophia Hober, Stockholm (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/845,817

(22) Filed: Sep. 4, 2015

(65) Prior Publication Data
US 2016/0152668 A1 Jun. 2, 2016

Related U.S. Application Data

(60) Division of application No. 13/488,662, filed on Jun. 5, 2012, now Pat. No. 9,156,892, which is a continuation of application No. 12/900,958, filed on Oct. 8, 2010, now Pat. No. 8,198,404, which is a continuation of application No. 10/508,625, filed as application No. PCT/SE03/00475 on Mar. 20, 2003, now Pat. No. 7,834,158.

(30) Foreign Application Priority Data

Mar. 25, 2002 (SE) ...................... 0200943

(51) Int. Cl.
| | |
|---|---|
| C07K 1/22 | (2006.01) |
| C07K 14/195 | (2006.01) |
| C07K 14/31 | (2006.01) |
| B01D 15/38 | (2006.01) |
| B01J 20/286 | (2006.01) |
| B01J 20/32 | (2006.01) |
| C07K 16/06 | (2006.01) |

(52) U.S. Cl.
CPC ........... *C07K 14/31* (2013.01); *B01D 15/3809* (2013.01); *B01J 20/286* (2013.01); *B01J 20/3244* (2013.01); *C07K 1/22* (2013.01); *C07K 14/195* (2013.01); *C07K 16/065* (2013.01); *Y10S 530/81* (2013.01); *Y10S 530/825* (2013.01)

(58) Field of Classification Search
CPC ..... B01D 15/3809; C07K 1/22; C07K 16/065; C07K 14/195; C07K 14/31; Y01S 530/81
USPC .......................................... 530/413, 825, 811
See application file for complete search history.

(56) References Cited

U.S. PATENT DOCUMENTS

| | | | | |
|---|---|---|---|---|
| 7,834,158 B2 * | 11/2010 | Hober | ................ | B01D 15/3809 |
| | | | | 530/388.4 |
| 8,198,404 B2 | 6/2012 | Hober | | |
| 8,728,828 B2 * | 5/2014 | Berg | ................... | G01N 33/558 |
| | | | | 210/656 |
| 9,051,375 B2 * | 6/2015 | Li | ....................... | B01D 15/3809 |
| 9,156,892 B2 * | 10/2015 | Hober | ................ | B01D 15/3809 |

OTHER PUBLICATIONS

Linhult et al., "Improving the Tolerance of a Protein A Analogue to Repeated Alkaline Exposures Using Bypass Mutagenesis Approach" Proteins: Structure, Function, and Bioinformatics 55:407-416 (2004).
Geiger et al., "Deamidation, Isomerization, and Racemization at Asparaginyl and Aspartyl Residues in Peptides", J. Biological Chemistry, 262:785-794 (Jan. 15, 1987).
Gulich et al., "Stability towards alkaline conditions can be engineered into a protein ligand", J. Biotechnology, 80:169-178 (2000).
Nilsson et al., "A syntehic IgG-binding domain based on staphylococcal protein A", Protein Engineering, 1:107-113 (1987).
Jendeberg et al., "Kinetic analysis of the interaction between protein A domain variants and human Fc using plasmon resonance detection", J. Molecular Recognition, 8:270-278 (1995).
Cedergren et al., "Mutational analysis of the interaction between staphylococcal protein A and human IgG-1", Protein Engineering, 6:441-448 (1993).
Karlstrom et al., "Dual labeling of the binding protein allows for specific fluorescence detection of native protein", Analytical Biochemisty, 295:22-30 (Aug. 1, 2001).

* cited by examiner

*Primary Examiner* — Lynn Bristol
(74) *Attorney, Agent, or Firm* — Wood IP LLC

(57) ABSTRACT

The present invention relates to an immunoglobulin-binding protein, wherein at least one asparagine residue has been mutated to an amino acid other than glutamine or aspartic acid, which mutation confers an increased chemical stability at pH-values of up to about 13-14 compared to the parental molecule. The protein can for example be derived from a protein capable of binding to other regions of the immunoglobulin molecule than the complementarity determining regions (CDR), such as protein A, and preferably the B-domain of Staphylococcal protein A. The invention also relates to a matrix for affinity separation, which comprises an immunoglobulin-binding protein as ligand coupled to a solid support, in which protein ligand at least one asparagine residue has been mutated to an amino acid other than glutamine.

18 Claims, 10 Drawing Sheets

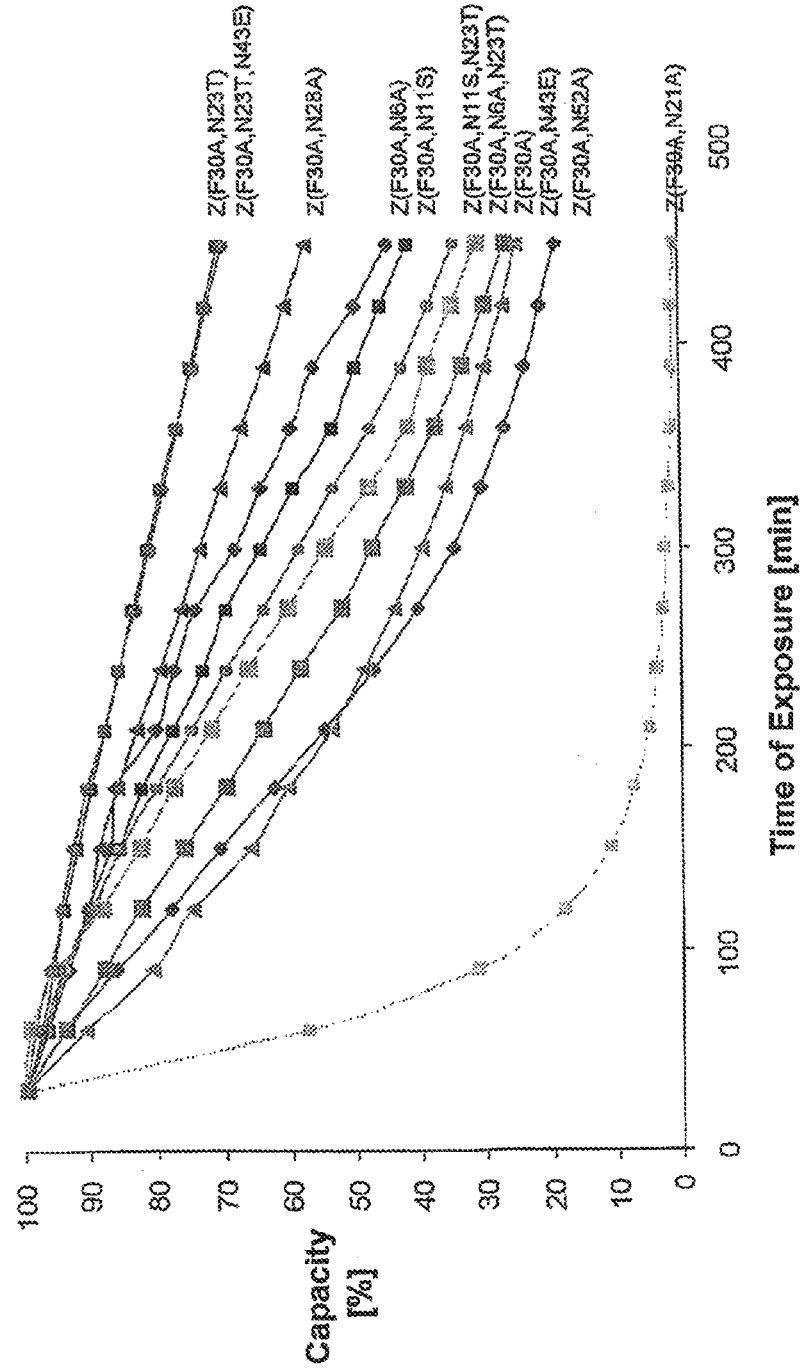

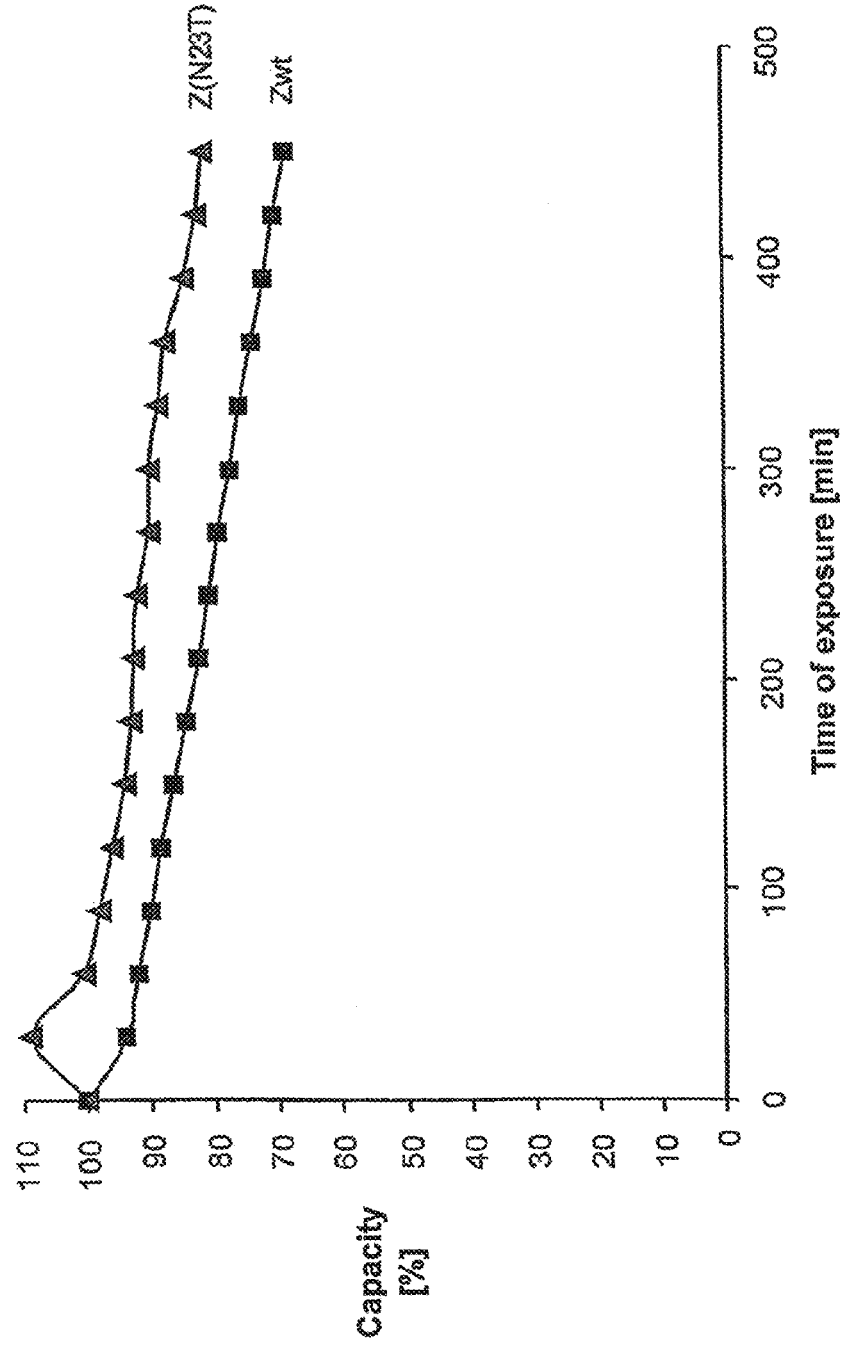

Figure 3:

```
        KpnI
        ~~~~~
              AccI
              ~~~~~
    L   G   T   V   D   A*  K   F   D*  K   E   Q   Q   N   A   F   Y   E   I   L
    CTG GGT ACC GTA GAC GCC AAA TTC GAC AAA GAA CAA CAA AAC GCG TTC TAT GAG ATC TTA
    GAC CCA TGG CAT CTG CGG TTT AAG CTG TTT CTT GTT GTT TTG CGC AAG ATA CTC TAG AAT

H   L   P   N   L   T*  E   E   Q   R   N   A   F   I   Q   S   L   K   D   D
    CAT TTA CCT AAC TTA ACT GAA GAA CAA CGA AAC GCC TTC ATC CAA AGT TTA AAA GAT GAC
    GTA AAT GGA TTG AAT TGA CTT CTT GTT GCT TTG CGG AAG TAG GTT TCA AAT TTT CTA CTG

P   S   Q   S   A   N   L   L   A   E   A   K   K   L   N   D   A   Q   A   P
    CCA AGC CAA AGC GCT AAC CTT TTA GCA GAA GCT AAA AAG CTA AAT GAT GCT CAG GCG CCG
    GGT TCG GTT TCG CGA TTG GAA AAT CGT CTT CGA TTT TTC GAT TTA CTA CGA GTC CGC GGC

PstI
              ~~~~~
    K   C   .   L   Q   L
    AAA TGC TAA CTG CAG CTC
    TTT ACG ATT GAC GTC GAG
```

Figure 4:

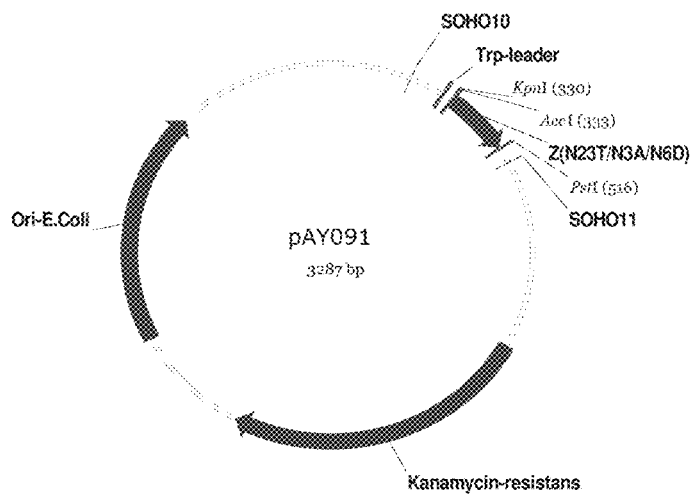

Figure 5:

```
                Acc1
                ----
         V   D   A*  K   F   D*  K   E   Q   Q   N   A   F   Y   E   I   L
    TTT TTT GTA GAC GCC AAA TTC GAC AAA GAA CAA CAA AAC GCG TTC TAT GAG ATC TTA
    AAA AAA CAT CTG CGG TTT AAG CTG TTT CTT GTT GTT TTG CGC AAG ATA CTC TAG AAT

H   L   P   N   L   T*  E   E   Q   R   N   A   F   I   Q   S   L   K   D   D
    CAT TTA CCT AAC TTA ACT GAA GAA CAA CGA AAC GCC TTC ATC CAA AGT TTA AAA GAT GAC
    GTA AAT GGA TTG AAT TGA CTT CTT GTT GCT TTG CGG AAG TAG GTT TCA AAT TTT CTA CTG

P   S   Q   S   A   N   L   L   A   E   A   K   K   L   N   D   A   Q   A   P
    CCA AGC CAA AGC GCT AAC CTT TTA GCA GAA GCT AAA AAG CTA AAT GAT GCT CAG GCG CCG
    GGT TCG GTT TCG CGA TTG GAA AAT CGT CTT CGA TTT TTC GAT TTA CTA CGA GTC CGC GGC

Acc1
         ----
    K   ~~~~~~~
    AAA GTA GAC AAA AAA
    TTT CAT CTG TTT TTT
```

Figure 6:

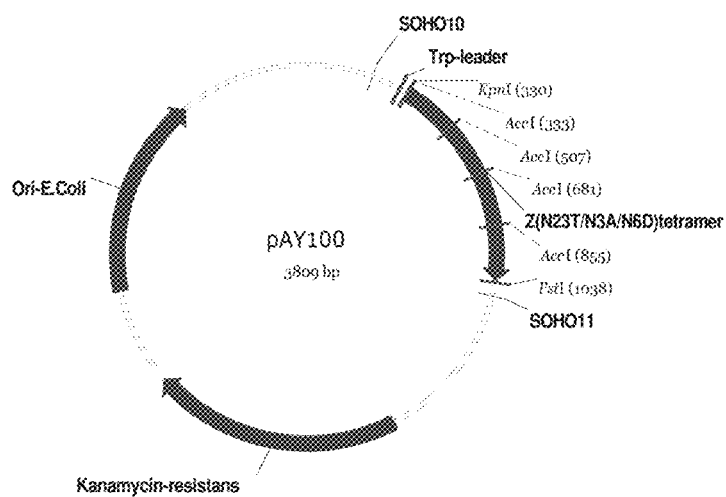

Figure 7:
```
AFFI-88:    PO₃²⁻-GCA GGG TAC CCT GCA
AFFI-89:            GGG TAC CCT GC
```
```
              KpnI
           --------
PO₃²⁻-GCAGGGTACC CTGCA
        CGTCCCATGG G
```
Figure 8:
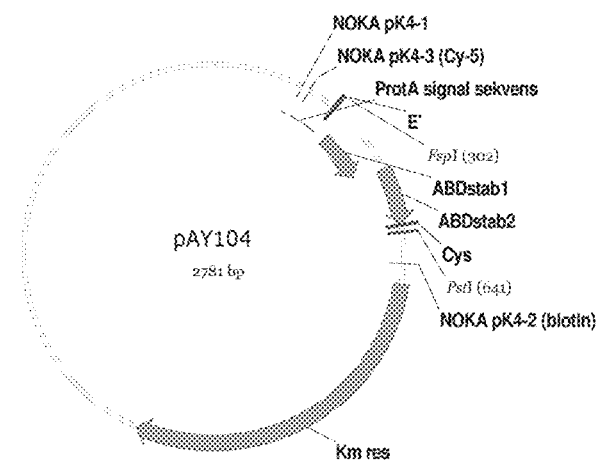
Figure 9:
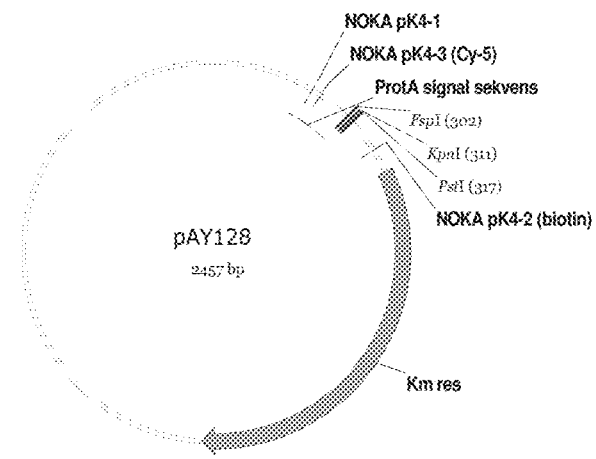

```
AFFI-90:    PO3²⁻-GCA ACA CGA TGA AGC CGG TAC CCT GCA
AFFI-91:           GGG TAC CGG CTT CAT CGT GTT GC
```

MUTATED IMMUNOGLOBULIN-BINDING PROTEIN

CROSS-REFERENCE TO RELATED APPLICATIONS

This application is a continuation of U.S. patent application Ser. No. 12/900,958 filed Oct. 8, 2010, now U.S. Pat. No. 8,198,404, which is a continuation of U.S. patent application Ser. No. 10/508,625 filed Sep. 20, 2004, now U.S. Pat. No. 7,834,158, which is a filing under 35 U.S.C. §371 and claims priority to international patent application number PCT/SE2003/000475 filed Mar. 20, 2003, published on Oct. 2, 2003 as WO 2003/080655, which claims priority to application number 0200943-9 filed in Sweden on Mar. 25, 2002.

FIELD OF THE INVENTION

The present invention relates to the field of mutant proteins, and more specifically to a mutant protein that exhibits improved stability compared to the parental molecule as well as to a method of producing a mutant protein according to the invention. The invention also relates to an affinity separation matrix, wherein a mutant protein according to the invention is used as an affinity ligand.

BACKGROUND OF THE INVENTION

A great number of applications in the biotechnological and pharmaceutical industry require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitising agent is NaOH, and the concentration thereof can range from 0.1 up to e.g. 1 M, depending on the degree and nature of contamination. NaOH is known to be an effective CIP agent achieving multilog reduction of contaminants, such as microbes, proteins, lipids and nucleic acids. Another advantage of NaOH is that it can easily be disposed of without any further treatment. However, this strategy is associated with exposing the matrix for pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focussed on the development of engineered protein ligands that exhibit an improved capacity to withstand alkaline pH-values. For example, Gülich et al (Susanne Gülich, Martin Linhult, Per-Åke Nygren, Mathias Uhlén, Sophia Hober, Journal of Biotechnology 80 (2000), 169-178: Stability towards alkaline conditions can be engineered into a protein ligand) suggested protein engineering to improve the stability properties of a Streptococcal albumin-binding domain (ABD) in alkaline environments. Previously, it was shown that structural modification, such as deamidation and cleavage of the peptide backbone, of asparagine and glutamine residues in alkaline conditions is the main reason for loss of activity upon treatment in alkaline solutions, and that asparagine is the most sensitive of the two (Geiger, T., and S. Clarke. 1987. Deamidation, Isomerization, and Racemization at Asparaginyl and Aspartyl Residues in Peptides. *J. Biol. Chem.* 262:785-794). It is also known that the deamidation rate is highly specific and conformation dependent (Kosky, A. A., U. O. Razzaq, M. J. Treuheit, and D. N. Brems. 1999. The effects of alpha-helix on the stability of Asn residues: deamidation rates in peptides of varying helicity. *Protein Sci.* 8:2519-2523; Kossiakoff, A. A. 1988. Tertiary structure is a principal determinant to protein deamidation. *Science.* 240:191-194; and Lura, R., and V. Schirch. 1988. Role of peptide conformation in the rate and mechanism of deamidation of asparaginyl residues. *Biochemistry.* 27:7671-7677), and the shortest deamidation half times have been associated with the sequences -asparagine-glycine- and -asparagine-serine. Accordingly, Gülich et al created a mutant of ABD, wherein all the four asparagine residues of native ABD have been replaced by leucine (one residue), asparte (two residues) and lysine (one residue). Further, Gülich et al report that their mutant exhibits a target protein binding behaviour similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Thus, the studies performed by Gülich et al were performed on a Streptococcal albumin-binding domain. However, affinity chromatography is also used in protocols for purification of other molecules, such as immunoglobulins, e.g. for pharmaceutical applications. A particularly interesting class of affinity reagents is proteins capable of specific binding to invariable parts of an antibody molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection. At present, SpA-based affinity medium probably is the most widely used affinity medium for isolation of monoclonal antibodies and their fragments from different samples including industrial feed stocks from cell cultures. Accordingly, various matrices comprising protein A-ligands are commercially available, for example, in the form of native protein A (e.g. Protein A SEPHAROSE™, GE Healthcare, Uppsala, Sweden) and also comprised of recombinant protein A (e.g. rProtein A SEPHAROSE™, GE Healthcare, Uppsala, Sweden). More specifically, the genetic manipulation performed in said commercial recombinant protein A product is aimed at facilitating the attachment thereof to a support.

Accordingly, there is a need in this field to obtain protein ligands capable of binding immunoglobulins, especially via the Fc-fragments thereof, which are also tolerant to one or more cleaning procedures using alkaline agents.

SUMMARY OF THE INVENTION

One object of the present invention is to provide a mutated immunoglobulin-binding protein ligand that exhibits an improved stability at increased pH-values, and accordingly an improved tolerance to cleaning under alkaline conditions, as compared to the parental molecule.

Another object of the invention is to provide such a protein ligand, which binds specifically to the Fc-fragment of immunoglobulins, such as IgG, IgA and/or IgM.

Yet another object of the invention is to provide a protein ligand as described above, which also exhibits an affinity which is retained for a longer period of time in alkaline conditions than that of the parental molecule.

A further object of the present invention is to provide an affinity separation matrix, which comprises mutant protein ligands capable of binding immunoglobulins, such as IgG, IgA and/or IgM, preferably via their Fc-fragments, which ligands exhibit an improved tolerance to cleaning under alkaline conditions, as compared to the parental molecule ligand.

One or more of the above-defined objects can be achieved as described in the appended claims.

BRIEF DESCRIPTION OF THE DRAWINGS

FIG. 2(a) and FIG. 2(b) illustrates the results obtained after alkaline treatment (cleaning-in-place) of mutant proteins according to the invention as compared to the destabilised protein Z. A comparison of the capacity after repeated CIP-treatment following an ordinary affinity chromatography scheme. 0.5 M NaOH was used as cleaning agent. The protocol was run 16 times and the duration for the alkaline sanitisation was 30 minutes in each round. FIG. 2(a) shows the inactivation pattern for Z(F30A) and variants thereof, whereas FIG. 2(b) shows the inactivation pattern for Zwt and Z(N23T).

FIG. 3 shows the gene encoding the Z(N23T/N3A/N6D)-Cys after insertion into vector as described in example 4(a). The mutations are marked with *.

FIG. 4 shows a plasmid map of the plasmid pAY91, which contains the gene encoding Z(N23T/N3A/N6D)-Cys as described in example 4(a).

FIG. 5 shows the gene encoding the Z(N23T/N3A/N6D) after insertion into vector as described in example 4(b). The mutations are marked with *.

FIG. 6 shows an example of plasmid map for the plasmid pAY100 expressing the tetramer of Z(N23T/N3A/N6D)-Cys as described in example 5.

FIG. 7 shows the adapter for introducing a KpnI-site into a vector with SPA promoter and signal sequence according to example 6.

FIG. 8 shows the plasmid pAY104, which contains SPA promoter and signal sequence to be used for introduction of an adapter containing a KpnI-site, as described in example 6.

FIG. 9 shows the resulting plasmid, pAY128, after insertion of the adapter according to example 6.

DEFINITIONS

Figure 1:
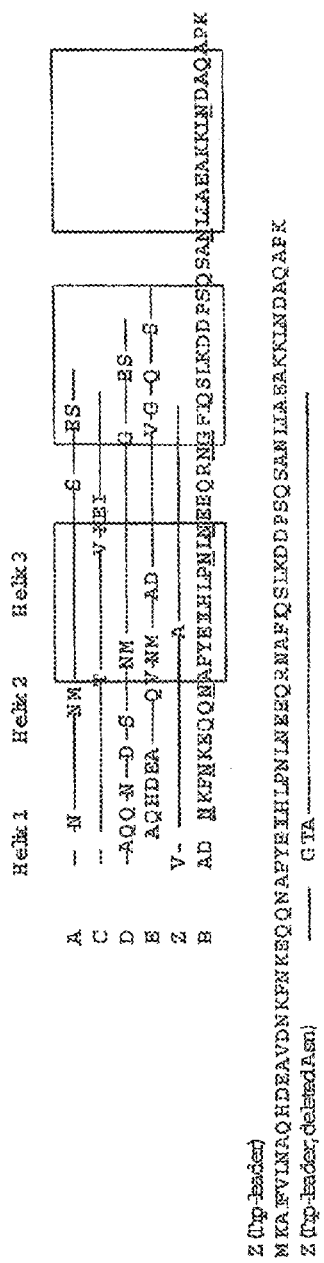
FIG. 1 shows amino acid alignments of the five homologous domains (E, D, A, B and C) of SpA. Horizontal lines indicate amino acid identity. The three boxes show the α-helices of $Z_{wt}$ as determined by Tashiro and co-workers (Tashiro et al., 1997). The asparagine residues, and also one glycine residue in the B domain, which were replaced, are underlined in the figure. Also, amino acid alignments for Zwt and Z(N23T) are shown.
Figure 10:
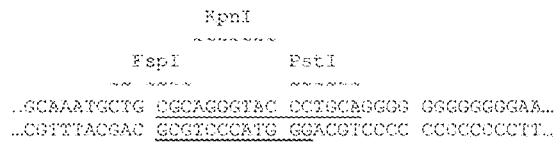
FIG. 10 shows the constructed cloning cassette of example 6, where the original adapter is underlined.
Figure 11:
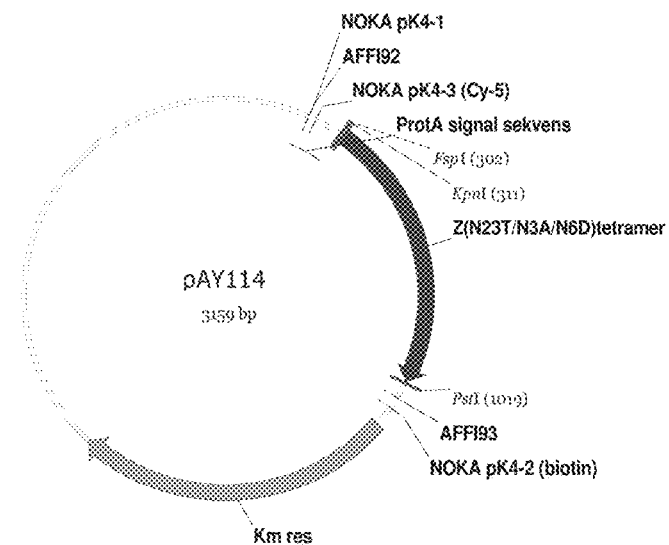
FIG. 11 shows plasmid pAY114 after insertion of the Z(N23T/N3A/N6D)-Cys-tetramer as described in Example 6.
Figure 12:
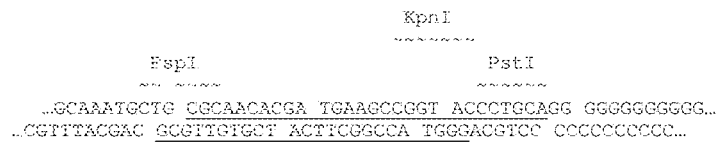
FIG. 12 shows the constructed cloning cassette of example 7, where the original adapter is underlined.
Figure 13:
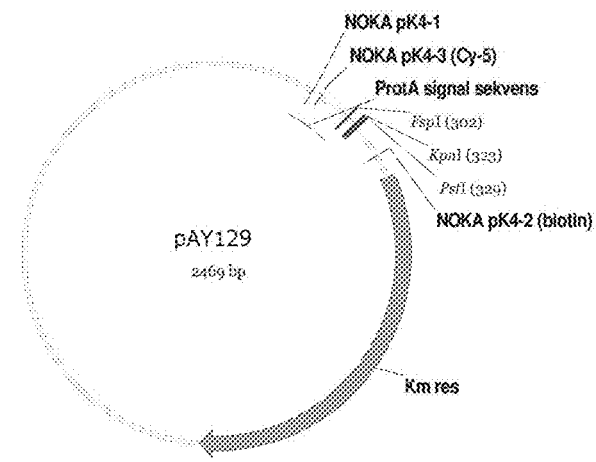
FIG. 13 shows the resulting plasmid, pAY129, after insertion of the adapter according to example 7.
Figure 14:
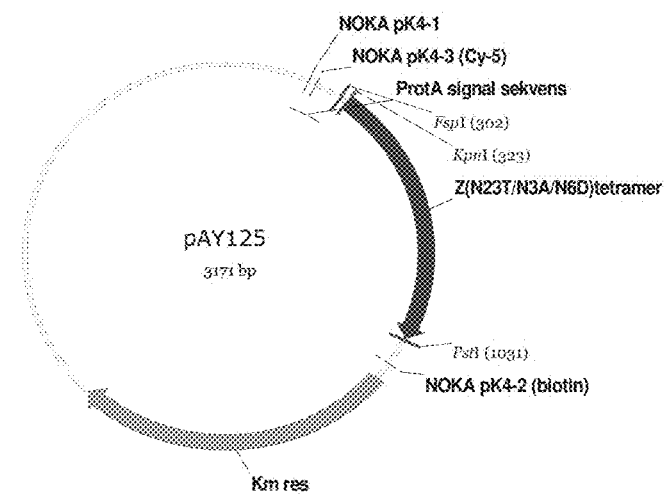
FIG. 14 shows plasmid pAY125 after insertion of the Z (N23T/N3A/N6D) tetramer-Cys as described in example 7.
Figure 15:
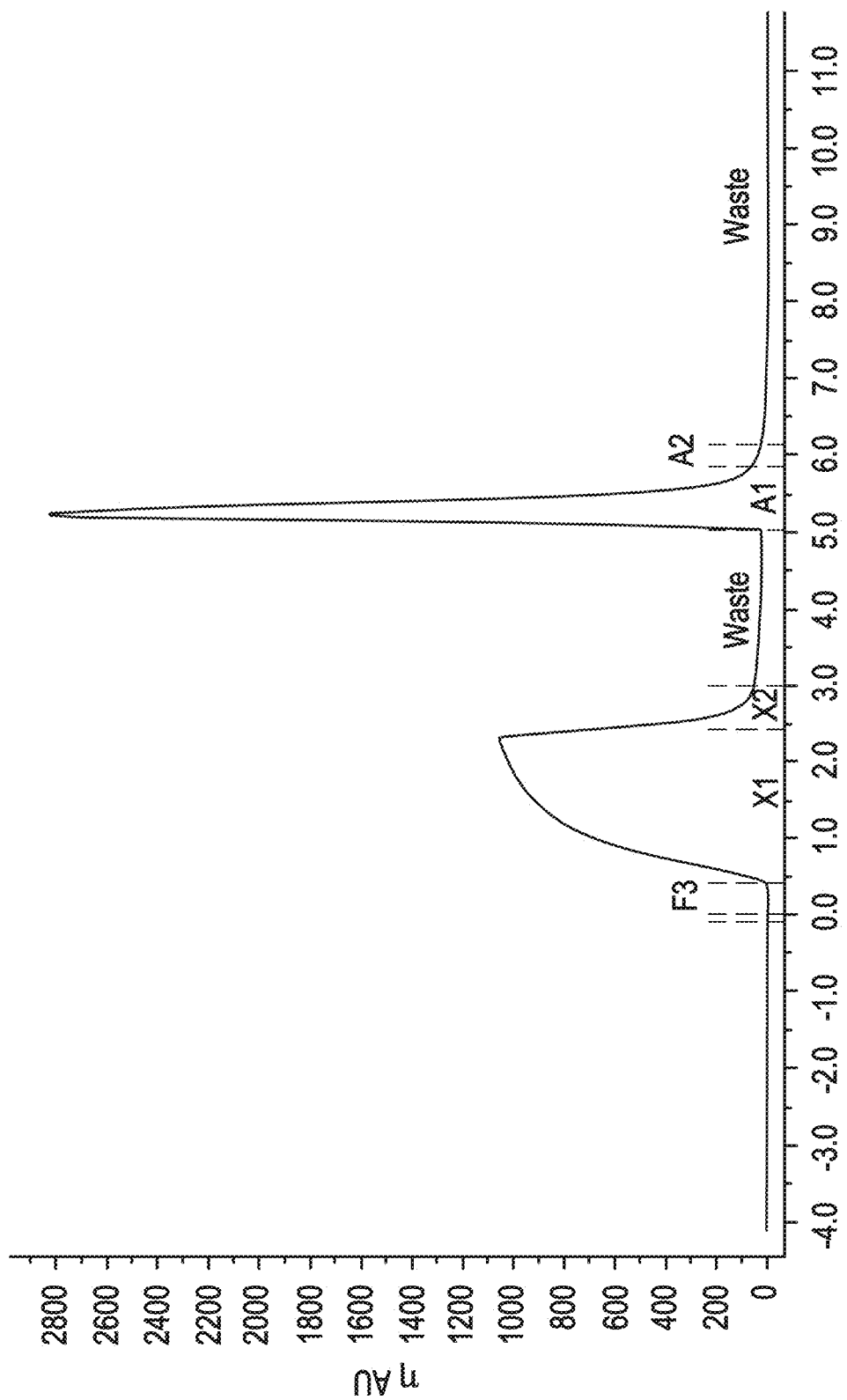
FIG. 15 is a chromatogram obtained from a separation of human IgG (hIgG), as described in example 8, where the first peak corresponds to the flow-through material and the second peak corresponds to eluted hIgG.

The term "protein" is used herein to describe proteins as well as fragments thereof. Thus, any chain of amino acids that exhibits a three dimensional structure is included in the term "protein", and protein fragments are accordingly embraced.

The term "functional variant" of a protein means herein a variant protein, wherein the function, in relation to the invention defined as affinity and stability, are essentially retained. Thus, one or more amino acids that are not relevant for said function may have been exchanged.

The term "parental molecule" is used herein for the corresponding protein in the form before a mutation according to the invention has been introduced.

The term "structural stability" refers to the integrity of three-dimensional form of a molecule, while "chemical stability" refers to the ability to withstand chemical degradation.

The term "Fc fragment-binding" protein means that the protein is capable of binding to the Fc fragment of an immunoglobulin. However, it is not excluded that an Fc fragment-binding protein also can bind other regions, such as Fab regions of immunoglobulins.

In the present specification, if not referred to by their full names, amino acids are denoted with the conventional one-letter symbols.

Mutations are defined herein by the number of the position exchanged, preceded by the wild type or non-mutated amino acid and followed by the mutated amino acid. Thus, for example, the mutation of an asparagine in position 23 to a threonine is denoted N23T.

DETAILED DESCRIPTION OF THE INVENTION

In one aspect, the present invention relates to an immunoglobulin-binding protein capable of binding to other regions of the immunoglobulin molecule than the complementarity determining regions (CDR), wherein at least one asparagine residue of a parental immunoglobulin-binding protein has been mutated to an amino acid other than glutamine, which mutation confers an increased chemical stability at alkaline pH-values compared to the parental molecule. The increased stability means that the mutated protein's initial affinity for immunoglobulin is essentially retained for a prolonged period of time, as will be discussed below.

The retained affinity for the target protein achieved according to the invention is in part due to a retained spatial conformation of the mutant protein. The affinity of mutated proteins to immunoglobulins can for example be tested by the skilled person using biosensor technology using for example a BIACORE™ 2000 standard set-up (Biacore AB, Uppsala, Sweden), as will be illustrated in the experimental part below. In this context, it is understood from the term "essentially" retained that the mutated protein exhibits an affinity for immunoglobulin which is of the same order of magnitude as that of the parental molecule. Accordingly, in an initial phase, the binding capacity of the mutated protein is comparable with that of the parental molecule. However, due to the below-discussed chemical stability of the mutated protein, which is retained in time, its binding capacity will decrease more slowly than that of the parental molecule in an alkaline environment. The environment can be defined as alkaline, meaning of an increased pH-value, for example above about 10, such as up to about 13 or 14, i.e. from 10-13 or 10-14, in general denoted alkaline conditions. Alternatively, the conditions can be defined by the concentration of NaOH, which can be up to about 1.0 M, such as 0.7 M or specifically about 0.5 M, accordingly within a range of 7-1.0 M.

The increased chemical stability of the mutated protein according to the invention can easily be confirmed by the skilled person in this field e.g. by routine treatment with NaOH at a concentration of 0.5 M, as will be described in the experimental part below. In this context, it is to be understood that similar to what is said above, an "increased" stability means that the initial stability is retained during a longer period of time than what is achieved by the parental molecule. Even though similar mutations have been reported for a Streptococcal albumin-binding domain (Gülich et al, see above), it is well known that the rate of the deamidation involved in protein susceptibility to degradation in alkaline environments is highly sequence and conformation dependent. Since the amino acid sequence of ABD comprises no amino acid sequence similarity to immunoglobulin-binding proteins such as the individual domains staphylococcal protein A, it would not appear as though the teachings of Gülich et al could be applied also to immunoglobulin-binding proteins. However, the present invention shows for the first time that mutation of one or more asparagine residues of an immunoglobulin-binding protein surprisingly provides an improved chemical stability and hence a decreased degradation rate in environments wherein the pH is above about 10, such as up to about 13 or 14.

Thus, the present invention provides a mutated protein, which is useful e.g. as a protein ligand in affinity chromatography for selective adsorption of immunoglobulins, such as IgG, IgA and/or IgM, preferably IgG, from a mammalian species, such as a human. The purpose of the adsorption can be either to produce a purified product, such as a pure immunoglobulin fraction or a liquid from which the immunoglobulin has been removed, or to detect the presence of immunoglobulin in a sample. The ligand according to the invention exhibits a chemical stability sufficient to withstand conventional alkaline cleaning for a prolonged period of time, which renders the ligand an attractive candidate for cost-effective large-scale operation where regeneration of the columns is a necessity.

Accordingly, in the protein according to the invention, one or more asparagine (N) residues have been mutated to amino acids selected from the group that consists of glycine (G), alanine (A), valine (V), leucine (L), isoleucine (I), serine (S), threonine (T), cysteine (C), methionine (M), phenylalanine (F), tyrosine (Y), tryptophan (W), glutamic acid (E), arginine (R), histidine (H), lysine (K) or proline (P), or any modified amino acid that is not susceptible to the undesired deamidation and isomerisation. Alternatively, one or more asparagine (N) residues have been mutated to glutamine (Q).

The immunoglobulin-binding protein can be any protein with a native immunoglobulin-binding capability, such as Staphylococcal protein A (SpA) or Streptococcal protein G (SpG). For a review of other such proteins, see e.g. Kronvall, G., Jonsson, K. Receptins: a novel term for an expanding spectrum of natural and engineered microbial proteins with binding properties for mammalian proteins, *J. Mol. Recognit.* 1999 January-February; 12(1):38-44. Review.

In one embodiment, the present invention is a mutated protein, which comprises at least the binding region of an immunoglobulin-binding protein and wherein at least one such asparagine mutation is present within said region. Accordingly, in this embodiment, a mutated protein according to the invention comprises at least about 75%, such as at least about 80% or preferably at least about 95%, of the sequence as defined in SEQ ID NO. 1 or 2, with the proviso that the asparagine mutation is not in position 21.

In the present specification, SEQ ID NO 1 defines the amino acid sequence of the B-domain of SpA and SEQ ID NO 2 defines a protein known as protein Z. Protein Z is synthetic construct derived from the B-domain of SpA, wherein the glycine in position 29 has been exchanged for alanine, and it has been disclosed in the literature, see e.g. Ståhl et al, 1999: Affinity fusions in biotechnology: focus on protein A and protein G, in The Encyclopedia of Bioprocess Technology: Fermentation, Biocatalysis and Bioseparation. M. C. Fleckinger and S. W. Drew, editors. John Wiley and Sons Inc., New York, 8-22. Further, protein Z has been used both as a ligand in affinity chromatography. However, even though protein Z exhibits an improved chemical stability to certain chemicals other than NaOH as compared to the SpA B-domain, it is still not as stable in conditions of increased pH-values as required to withstand the many CIP regeneration steps desired in an economic industrial plant.

In one embodiment, the above described mutant protein is comprised of the amino acid sequence defined in SEQ ID NO 1 or 2, or is a functional variant thereof. The term "functional variant" as used in this context includes any similar sequence, which comprises one or more further variations in amino acid positions that have no influence on the mutant protein's affinity to immunoglobulins or its improved chemical stability in environments of increased pH-values.

In an advantageous embodiment, the present mutation(s) are selected from the group that consists of N23T; N23T and N43E; N28A; N6A; N11S; N11S and N23T; and N6A and N23T; and wherein the parental molecule comprises the sequence defined by SEQ ID NO 2. As mentioned above, in order to achieve a mutant protein useful as a ligand with high binding capacity for a prolonged period of time in alkaline conditions, mutation of the asparagine residue in position 21 is avoided. In one embodiment, the asparagine residue in position 3 is not mutated.

In the most advantageous embodiment, in the present protein, an asparagine residue located between a leucine residue and a glutamine residue has been mutated, for example to a threonine residue. Thus, in one embodiment, the asparagine residue in position 23 of the sequence defined in SEQ ID NO 2 has been mutated, for example to a threonine residue. In a specific embodiment, the asparagine residue in position 43 of the sequence defined in SEQ ID NO 2 has also been mutated, for example to a glutamic acid. In the embodiments where amino acid number 43 has been mutated, it appears to most advantageously be combined with at least one further mutation, such as N23T.

The finding according to the invention that the various asparagine residues of the B-domain of SpA and protein Z can be ascribed different contributions to affinity and stability properties of the mutated protein was quite unexpected, especially in view of the above discussed teachings of Gülich et al wherein it was concluded that all the asparagine residues of ABD could be mutated without any internal discrimination.

Thus, the invention encompasses the above-discussed monomeric mutant proteins. However, such protein monomers can be combined into multimeric proteins, such as dimers, trimers, tetramers, pentamers etc. Accordingly, another aspect of the present invention is a multimer comprised of at least one of the mutated proteins according to the invention together with one or more further units, preferably also mutant proteins according to the invention. Thus, the present invention is e.g. a dimer comprised of two repetitive units.

In one embodiment, the multimer according to the invention comprises monomer units linked by a stretch of amino acids preferably ranging from 0 to 15 amino acids, such as 5-10. The nature of such a link should preferably not destabilise the spatial conformation of the protein units. Furthermore, said link should preferably also be sufficiently stable in alkaline environments not to impair the properties of the mutated protein units.

In the best embodiment at present, the multimer is a tetramer of protein Z comprising the mutation N23T, wherein the length of the linking units are 5-10 amino acids. In one embodiment, the present multimer comprises the sequence VDAKFN-Z(N23T)-QAPKVDAKFN-Z(N23T) QAPKC. In another embodiment, the multimer comprises the sequence VDAKFD-Z(N23T)-QAPKVDAKFD-Z (N23T)-ZQAPKC.

In a specific embodiment, the present multimer also comprises one or more of the E, D, A, B, and C domains of Staphylococcal protein A. In this embodiment, it is preferred that asparagine residues located in loop regions have been mutated to more hydrolysis-stable amino acids. In an embodiment advantageous for structural stability reasons, the glycine residue in position 29 of SEQ ID NOS. 1 has also been mutated, preferably to an alanine residue. Also, it is advantageous for the structural stability to avoid mutation of the asparagine residue in position 52, since it has been found to contribute to the α-helical secondary structure content of the protein A molecule.

In a further aspect, the present invention relates to a nucleic acid encoding a mutant protein or multimer as described above. Accordingly, the invention embraces a DNA sequence that can be used in the production of mutant protein by expression thereof in a recombinant host according to well-established biotechnological methods. Consequently, another aspect of the present invention is an expression system, which enables production of a mutant protein as described above. Bacterial hosts can conveniently be used, e.g. as described in the experimental part below. In an alternative embodiment, the present invention is a cell line that has been genetically manipulated to express a mutant protein according to the invention. For methods to this end, see e.g. Sambrook et al., Molecular Cloning: A Laboratory Manual ($2^{nd}$ ed), vols. 1-3, Cold Spring Harbor Laboratory, (1989).

Naturally, once the desired sequence has been established, the mutant protein according to the invention can alternatively be produced by synthetic methods.

Accordingly, the present invention also includes a biotechnological or synthetic method of producing a mutant protein or a multimer according to the invention.

In another aspect, the present invention relates to a matrix for affinity separation, which matrix comprises ligands that comprise immunoglobulin-binding protein coupled to a solid support, in which protein at least one asparagine residue has been mutated to an amino acid other than glutamine. The present matrix, when compared to a matrix comprised of the parental molecule as ligand, exhibits an increased binding capacity during two or more separations with intermittent alkaline cleaning. The mutated protein ligand is preferably an Fc-fragment-binding protein, and can be used for selective binding of IgG, IgA and/or IgM, preferably IgG.

The matrix according to the invention can comprise the mutant protein as described above in any embodiment thereof as ligand. In the most preferred embodiment, the ligands present on the solid support comprise a multimer as described above.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo- or polyethylenoxy groups on their external and, if present, also on internal surfaces. In one embodiment, the polymers may, for instance, be based on polysaccharides, such as dextran, starch, cellulose, pullulan, agarose etc, which advantageously have been cross-linked, for instance with bisepoxides, epihalohydrins, 1,2,3-trihalo substituted lower hydrocarbons, to provide a suitable porosity and rigidity. In the most preferred embodiment, the solid support is porous agarose beads. The supports used in the present invention can easily be prepared according to standard methods, such as inverse suspension gelation (S Hjertén: Biochim Biophys Acta 79(2), 393-398 (1964). Alternatively, the base matrices are commercially available products, such as SEPHAROSE™ FF (GE Healthcare, Uppsala, Sweden). In an embodiment, which is especially advantageous for large-scale separations, the support has been adapted to increase its rigidity, and hence renders the matrix more suitable for high flow rates.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare, Uppsala, Sweden) is used.

In another alternative, the solid support according to the invention comprises a support of inorganic nature, e.g. silica, zirconium oxide etc.

In yet another embodiment, the solid support is in another form such as a surface, a chip, capillaries, or filter.

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

The ligand may be attached to the support via conventional coupling techniques utilising, e.g. amino and/or carboxy groups present in the ligand. Bisepoxides, epichlorohydrin, CNBr, N-hydroxysuccinimide (NHS) etc are well-known coupling reagents. Between the support and the ligand, a molecule known as a spacer can be introduced, which will improve the availability of the ligand and facilitate the chemical coupling of the ligand to the support. Alternatively, the ligand may be attached to the support by non-covalent bonding, such as physical adsorption or biospecific adsorption.

In an advantageous embodiment, the present ligand has been coupled to the support by thioether bonds. Methods for performing such coupling are well-known in this field and easily performed by the skilled person in this field using standard techniques and equipment. In an advantageous embodiment, the ligand is firstly provided with a terminal cysteine residue for subsequent use in the coupling. The skilled person in this field also easily performs appropriate steps of purification.

As mentioned above, the affinity to immunoglobulin i.e. the binding properties of the present ligand, and hence the capacity of the matrix, is not essentially changed in time by treatment with an alkaline agent. Conventionally, for a cleaning in place treatment of an affinity separation matrix, the alkaline agent used is NaOH and the concentration thereof is up to 0.75 M, such as 0.5 M.

Thus, another way of characterising the matrix according to the invention is that due to the above discussed mutations, its binding capacity will decrease to less than about 70%, preferably less than about 50% and more preferably less than about 30%, such as about 28%, after treatment with 0.5 M NaOH for 7.5 h.

In a further aspect, the present invention relates to a method of isolating an immunoglobulin, such as IgG, IgA and/or IgM, wherein a mutant protein, a multimer or a matrix according to the invention is used. Thus, the invention encompasses a process of chromatography, wherein at least one target compound is separated from a liquid by adsorption to a mutant protein or a multimer or matrix described above. The desired product can be the separated compound or the liquid. Thus, this aspect of the invention relates to affinity chromatography, which is a widely used and well-known separation technique. In brief, in a first step, a solution comprising the target compounds, preferably antibodies as mentioned above, is passed over a separation matrix under conditions allowing adsorption of the target compound to ligands present on said matrix. Such conditions are controlled e.g. by pH and/or salt concentration i.e. ionic strength in the solution. Care should be taken not to exceed the capacity of the matrix, i.e. the flow should be sufficiently slow to allow a satisfactory adsorption. In this step, other components of the solution will pass through in principle unimpeded. Optionally, the matrix is then washed, e.g. with an aqueous solution, in order to remove retained and/or loosely bound substances. The present matrix is most advantageously used with a washing step utilising an alkaline agent, as discussed above. In a next step, a second solution denoted an eluent is passed over the matrix under conditions that provide desorption i.e. release of the target compound. Such conditions are commonly provided by a change of the pH, the salt concentration i.e. ionic strength, hydrophobicity etc. Various elution schemes are known, such as gradient elution and step-wise elution. Elution can also be provided by a second solution comprising a competitive substance, which will replace the desired antibody on the matrix. For a general review of the principles of affinity chromatography, see e.g. Wilchek, M., and Chaiken, I. 2000. An overview of affinity chromatography. *Methods Mol. Biol.* 147: 1-6.

In an alternative embodiment, a mutant protein according to the invention is used as a lead compound in a process wherein an organic compound is modelled to resemble its three dimensional structure. The so modelled compound is known as a mimetic. Mimetic design, synthesis and testing can be used to avoid randomly screening large number of molecules. In brief, such a method can involve determining the particular parts of the protein that are critical and/or important for a property such as immunoglobulin-binding. Once these parts have been identified, its structure is modelled according to its physical properties, e.g. stereochemistry, bonding, size, charge etc using data from a range of sources, such as spectroscopic techniques, X-ray diffraction data and NMR. Computational analysis, similarity mapping and other techniques can be used in this process Important considerations in this kind of process are the ease to synthesise a compound, pharmacological acceptance, degradation pattern in vivo etc.

Finally, the present invention also comprises other uses of the mutant protein described above, such as in analytical methods, for medical purposes, e.g. for diagnosis, in arrays etc.

EXAMPLES

Below, the present invention will be described by way of examples, which are provided for illustrative purposes only and accordingly are not to be construed as limiting the scope of the present invention as defined by the appended claims. All references given below and elsewhere in this application are hereby included herein by reference.

In this part, since Z in its original form already has a significant but non-sufficient stability towards alkaline treatment, it was assumed that small changes in stability due to the mutations would be difficult to assess in laboratory testings. Therefore, a suppressor mutation method (Kotsuka, T., S. Akanuma, M. Tomuro, A. Yamagishi, and T. Oshima. 1996. Further stabilisation of 3-isopropylmalate dehydrogenase of an extreme thermophile, *Thermus thermophilus*, by a suppressor mutation method. *J Bacteriol.* 178:723-727; and Sieber, V., A. Plückthun, and F. X. Schmidt 1998. Selecting proteins with improved stability by a phage-based method. *Nature Biotechnology.* 16:955-960) was used to provide a variant of the Z domain with a decreased structural stability. According to this strategy the destabilised variant of protein Z, herein denoted Z(F30A) (Cedergren et al., 1993, supra) was used as scaffold for subsequent introduction of additional mutations related to investigations of alkaline stability. The binding properties of this variant are similar to native protein Z, since F30 is not involved in the Fc-binding.

Further, Zwt denotes the wild type Z domain, not containing the F30A substitution.

Experimental Strategy

To analyze which asparagines in the Z domain that are responsible for its instability in alkaline conditions, a mutational analysis was performed. In order to enable detection of improvements regarding the alkaline stability of the Z domain, it was decided to use a mutated variant, Z(F30A), since the Z-domain already possesses a significant but non-sufficient stability towards alkaline conditions. Z(F30A) has earlier been shown to possess an affinity to IgG that is similar to the wild type, but also a remarkably decreased structural stability due to the mutation of an amino acid that normally takes part in the hydrophobic core (Cedergren et al., 1993, supra; Jendeberg, L., B. Persson, R. Andersson, R. Karlsson, M. Uhlen, and B. Nilsson. 1995. Kinetic analysis of the interaction between protein A domain variants and human Fc using plasmon resonance detection. *Journal of Molecular Recognition.* 8:270-278). The Z-domain is a three-helix bundle consisting of 58 amino acids, including eight asparagines (N3, N6, N11, N21, N23, N28, N43 and N52) (FIG. 1) (Nilsson, B., T. Moks, B. Jansson, L. Abrahmsen, A. Elmblad, E. Holmgren, C. Henrichson, T. A. Jones, and M. Uhlen. 1987. A synthetic IgG-binding domain based on staphylococcal protein A. *Protein Eng.* 1:107-113). To evaluate the effect of the different asparagines on the deactivation rate in alkaline conditions, seven of these residues were exchanged for other amino acids. Since N3 is located in the flexible amino-terminal of the domain, it was excluded from the study. It was assumed that a degradation of this amino acid would not affect the activity of a monomeric ligand and would therefore not be detectable in the present assay, which measures the retained activity. Moreover, since the amino acid is located outside the structured part of the domain it will presumably be easily replaceable during a multimerisation of the domain to achieve a protein A-like molecule. To facilitate the protein design, a comparison with the homologous sequences from the other domains of protein A was made (FIG. 1). From the comparison, it was decided to exchange asparagine 11 for a serine and 23 for threonine and finally 43 for a glutamic acid. Asparagine 6 was exchanged for alanine since the alternative when looking on the homologous sequences was aspartic acid, which also has been reported to be sensitive in alkaline conditions. All five domains of protein A have asparagines in the other positions (21, 28, 52). Hence, they were exchanged for alanines.

Example 1

Mutagenesis, Expression and Purification of Mutant Protein Z

Materials and Methods

Site-directed mutagenesis was performed using a two-step PCR-technique (Higuchi et al., 1988). Plasmid pDHZF30A (Cedergren et al., 1993) was used as template. Oligonucleotides coding for the different asparagine replacements and the A29G replacement were synthesised by Interactiva (Interactiva Biotechnologie GmbH, Ulm, Germany). The restriction enzymes XbaI and HindIII (MBI Fermentas Inc, Amhurst, N.Y.) were used for cloning into the vector pDHZ (Jansson et al., 1996) that was performed according to Sambrook (Sambrook et al., 1987). To create pTrpZ, the Z domain was amplified by PCR, using plasmid pKN1 as template (Nord et al., 1995). The fragment was restricted with XbaI and PstI and ligated into the vector pTrpABDT1T2 (Kraulis et al., 1996) that had been restricted with same enzymes. A MEGABACE™ 1000 DNA Sequencing System (GE Healthcare, Uppsala, Sweden) was used to verify correct sequence of inserted fragments. MEGABACE™ terminator chemistry (GE Healthcare, Uppsala, Sweden) was utilised according to the supplier's recommendations in a cycle sequencing protocol based on the dideoxy method (Sanger et al., 1977). During cloning procedures, *Escherichia coli* strain RR1ΔM15 (American Type Culture Collection, Rockville, Mass.) was used, whereas for expression of the different gene products 017 (Olsson, M. O., and L. A. Isaksson. 1979. Analysis of rpsD Mutations in *Escherichia coli*. I: Comparison of Mutants with Various Alterations in Ribosomal Protein S4. *Molec. gen. Genet.* 169:251-257) was used.

Production and purification of Z(F30A) and the different constructs thereof were performed according to the protocol outlined by Gülich (Gülich et al., 2000b, see above). The production of Z and pZ(N23T) were performed as described in Kraulis et al (Kraulis, P. J., P. Jonasson, P.-Å. Nygren, M. Uhlén, L. Jendeberg, B. Nilsson, and J. Kördel. 1996. The serum albumin-binding domain of streptococcal proteinG is a three-helix bundel: a heteronuclear NMR study. *FEBS lett.* 378:190-194). Relevant fractions were lyophilised. The amount of protein was estimated by absorbance measurements at 280 nm using the specific absorbance coefficient, a (1 g$^{-1}$ cm$^{-1}$), Z 0.156; Z(N23T), 0.169; Z(F30A), Z(F30A,N43E), Z(F30A,N23T,N43E) 0.157; Z(F30A,N6A), Z(F30A,N11S), Z(F30A,N21A), Z(F30A,N23T), Z(F30A,N28A), Z(F30A,N52A), Z(F30A,N6A,N23T), Z(F30A,N11S,N23T) 0.158. The concentration was confirmed by amino acid analysis (BMC, Uppsala, Sweden). The homogeneity was analysed by Sodium Dodecyl Sulfate PolyAcrylamide Gel Electrophoresis (SDS-PAGE) (Laemmli, U. K. 1970. Cleavage of Structural Proteins during the Assembly of the Head of Bacteriophage T4. *Nature.* 227:680-685) using the PHAST™ system. Lyophilised proteins were loaded on high-density gels (GE Healthcare, Uppsala, Sweden) under reducing conditions and stained with Coomassie Brilliant Blue according to the supplier's recommendations. The homogeneity and the molecular weights were further confirmed by mass spectrometry.

For CD spectroscopy, protein samples were prepared in a phosphate buffer (8.1 mM K$_2$HPO$_4$, 1.9 mM KH$_2$PO$_4$, pH 7.5) to a concentration of 10 μM. Spectra were recorded using a J-720 spectropolarimeter (JASCO, Tokyo, Japan) in the far UV region from 250 to 200 nm at RT in a quartz cell of path length 0.1 cm and with a scan speed of 10 nm min$^{-1}$ Each spectrum was the mean of five accumulated scans and the final spectra were converted into mean residue ellipticity (MRE) (deg cm$^2$ dmol$^{-1}$).

Results (Example 1)

All Z variants were successfully produced intracellular in *E. coli* at 37° C. and show the same expression levels, approximately 50 mg/l as estimated from SDS-PAGE. The proteins were all purified by IgG affinity chromatography. After the purification, samples were analysed with SDS-PAGE (data not shown), lyophilised and stored for further analyses. The molecular mass for protein Z and the different mutants thereof were also confirmed by mass spectrometry. The data confirmed correct amino acid content for all mutants (data not shown). Also, structural analyses were performed on a Circular Dichroism (CD) equipment, since it previously has been proven to be suitable for detecting structural changes in α-helical proteins (Johnson, C. W., Jr. 1990. Protein secondary structure and circular dichroism: a practical guide. *Proteins*. 7:205-214; and Nord, K., J. Nilsson, B. Nilsson, M. Uhlén, and P.-Å. Nygren. 1995. A combinatorial library of an α-helical bacterial receptor domain. *Prot. eng*. 8:601-608). All spectra show a minimum at 208 nm and at 222 nm in combination with a maximum around 195 nm, indicating a similar structure for the mutants and the parental molecule. However, Z(F30A,N52A) seems to have a somewhat lower α-helicity than the wild type Z and the other mutants thereof (data not shown).

Example 2

Biospecific Interaction Analysis

Materials and Methods

Differences in affinity and kinetic constants of the association and dissociation states were detected on a BIACORE™ 2000 instrument (Biacore AB, Uppsala, Sweden). Human polyclonal IgG and HSA (negative reference) were immobilised by amine coupling on the carboxylated dextran layer of a CM5 sensor chip (Biacore AB) according to the supplier's recommendations. The immobilisation of IgG resulted in approximately 2000 RU. Z, ZF30A, and the different mutants were prepared in HBS (10 mM HEPES, 0.15 M NaCl, 3.4 mM EDTA, 0.005% surfactant P20, pH 7.4) at 10 different concentrations (100-550 nM). The samples were injected over the surfaces as duplicates in random order at a flow rate of 30 µl min$^{-1}$ 10 mM HCl was used to regenerate the surface. The data was analysed using the BIA evaluation 3.0.2b software (Biacore AB). The signals from a control surface immobilized with HSA were subtracted from the IgG surface. A 1:1 Langmuir model was assumed and apparent kinetic constants and also affinity constants were calculated. Also, the change in free binding energy ($\Delta\Delta G = -RT \ln K_{aff,mutant}/K_{aff,native}$) in relation to the native molecule was calculated.

Results (Example 2)

To determine the differences in affinity for the Z variants towards IgG, surface plasmon resonance (SPR) using a BIACORE™ was carried out. The aim was to compare the affinity for the different mutated Z variants according to the invention with the parental molecule. As mentioned above, due to the high alkaline stability of the parental Z domain it was decided to use a structurally destabilised variant of Z including the F30A mutation (Cedergren, L., R. Andersson, B. Jansson, M. Uhlén, and B. Nilsson. 1993. Mutational analysis of the interaction between staphylococcal protein A and human IgG$_1$. *Protein eng*. 6:441-448). Therefore, it was of importance to first confirm that the affinity between the mutated molecule and IgG was retained despite the mutation. As can be seen in table 1 below, the affinity of Z(F30A) is not significantly affected. The very small change in affinity gives a slightly higher stability to the complex of Z(F30A) and IgG compared to the parental molecule Z and IgG. This is in accordance with results earlier reported by Jendeberg et al. (Cedergren et al., 1993, supra; Jendeberg et al., 1995, supra). All mutants constructed with Z(F30A) as scaffold were analysed and compared with their parental molecule (Z(F30A)). The results show that the overall affinity is not significantly affected by the mutations, indicating that none of the asparagine mutations according to the invention are very important for the binding to IgG (see table 1 below). In all Z variants including the N21A or the N43E mutation, only a slightly lower affinity constant was observed. For mutants with the N23T mutation, surprisingly, the affinity even seems to be slightly higher. Also, in the case of the N28A-mutation, the decrease in affinity is very small, and cannot be expected to have any essential influence if the mutant protein is used e.g. as a protein ligand. Furthermore, all constructs including the N28A-mutation have a remarkably increased off-rate. For the mutants including the N23T mutation the somewhat increased affinity seems to be due to a slightly increased on-rate. Also, the N6A-mutation gives a higher on-rate, but the affinity constant is not affected because of the increased off-rate that also follows the mutation.

TABLE 1

An overview of the kinetic study on the different Z domains carried out using the BIACORE™

| Mutant | kon [10$^5$ M$^{-1}$ s$^{-1}$] | koff [10$^{-3}$ s$^{-1}$] | Kaff [110$^7$ M$^{-1}$] | ΔΔG (vs Zwt) [kcal/mol] | ΔΔG (vs Z(F30A)) [kcal/mol] |
|---|---|---|---|---|---|
| Zwt | 1.5 | 3.7 | 4.0 | 0 | |
| Z(N23T) | 2.7 | 3.9 | 7 | −0.3 | |
| Z(F30A) | 1.9 | 4.17 | 4.5 | −0.1 | 0.0 |
| Z(F30A, N6A) | 7 | 21 | 3.3 | 0.1 | 0.2 |
| Z(F30A, N11S) | 1.6 | 4.9 | 3.2 | 0.1 | 0.2 |
| Z(F30A, N21A) | 1 | 3.8 | 2.6 | 0.3 | 0.4 |
| Z(F30A, N23T) | 2.1 | 3.75 | 5.6 | −0.2 | −0.1 |
| Z(F30A, N28A) | 3.1 | 9.87 | 3.2 | 0.1 | 0.2 |
| Z(F30A, N43E) | 1.3 | 5.1 | 2.6 | 0.3 | 0.4 |
| Z(F30A, N52A) | 1.5 | 4.9 | 3 | 0.2 | 0.3 |
| Z(F30A, N23T, N43E) | 0.8 | 3.8 | 2 | 0.4 | 0.5 |

$Z_{wt}$ was used as an internal standard during the different measurements. The differences in free binding energy are calculated relative to Zwt and Z(F30A) respectively.

Example 3

Stability Towards Alkaline Conditions

Materials and Methods

The behaviour of the variants of domain Z as affinity ligands was analysed by immobilisation to a standard affinity matrix. Z, Z(F30A), and mutated variants were covalently coupled to HITRAP™ affinity columns (GE Healthcare, Uppsala, Sweden) using the N-hydroxysuccinimide chemistry according to the manufacturer's recommendations. The columns were pulsed with TST and 0.2 M HAc, pH 3.1. Human polyclonal IgG in TST was prepared and injected onto the columns in excess. A standard affinity chromatography protocol was followed for 16 cycles on the ÄKTA™ Explorer 10 (GE Healthcare, Uppsala, Sweden). Between each cycle a CIP-step was integrated. The cleaning agent was 0.5 M NaOH and the contact time for each pulse was 30 minutes, resulting in a total exposure time of 7.5 hours. Eluted material was detected at 280 nm.

Results (Example 3)

Z, Z(F30A), and mutants thereof were covalently attached to HITRAP™ columns using NHS-chemistry. IgG in excess was loaded and the amount of eluted IgG was measured after each cycle to determine the total capacity of the column. Between each cycle the columns were exposed to CIP treatment consisting of 0.5 M NaOH. After 16 pulses, giving a total exposure time of 7.5 hours, the column with the Z(F30A)-matrix shows a 70% decrease of the capacity. The degradation data in FIG. 2a suggest that four of the exchanged asparagines (N6, N11, N43 and N52) are less sensitive to the alkaline conditions the mutants are exposed for in this experiment. In contrast, N23 seems to be very important for the stability of Z(F30A). Z(F30A,N23T) shows only a 28% decrease of capacity despite the destabilising F30A-mutation. Hence, the Z(F30A,N23T) is almost as stable as Zwt and thereby the most stabilised variant with Z(F30A) as scaffold. Also the Z(F30A)-domain with two additional mutations Z(F30A,N23T,N43E) shows the same pattern of degradation as Z(F30A,N23T). An exchange of N28 to an alanine also improves the stability of Z(F30A) towards alkaline conditions. Surprisingly, the column with Z(F30A,N21A) as affinity ligand reveals a dramatic loss of capacity when exposed to NaOH compared to the parental molecule. These data make Z(N23T) to a very advantageous candidate as ligand in affinity purification of IgG.

To finally prove the reliability of the strategy using a structurally destabilised variant of a molecule in order to make small changes in stability detectable, the N23T-mutation was grafted into the parental Z-domain. Both the parental Z-domain and Z(N23T) were coupled to HITRAP™-columns and exposed to alkaline conditions in the same way as for the already mentioned mutants. As can be seen in FIG. 2b, the Z(N23T)-mutant shows higher stability than Zwt when exposed to high pH.

Example 4

Construction of Monomers of Z-Mutants with and without a C-Terminal Cysteine

Three different mutations were introduced in a gene encoding Z(N23T): K4G, N3A and the double-mutation N3A/N6D.

The mutations were originally introduced into two different vectors: one with a cysteine in the C-terminus and one without the cysteine. This was done to later facilitate the construction of multimers with one single C-terminal cysteine.

Example 4(a)

Cysteine-Containing Monomer Construction

As template for the construction, a plasmid denoted "pGEM ZN23T", was used. This already contained the N23T-mutation in the Z-gene.

A PCR-reaction was performed with this plasmid as template and the two oligonucleotides

AFFI-63:
TTT TTT GTA GAC AAC GGA TTC AAC AAA GAA C

GRTO-40:
GAT CTG CTG CAG TTA GCA TTT CGG CGC CTG AGC ATC ATT TAG for the K4G-mutation,

AFFI-64:
TTT TTT GTA GAC GCC AAA TTC AAC AAA GAA C

GRTO-40:
GAT CTG CTG CAG TTA GCA TTT CGG CGC CTG AGC ATC ATT TAG for the N3A-mutation and,

AFFI-65:
TTT TTT GTA GAC GCC AAA TTC GAC AAA GAA C

GRTO-40:
GAT CTG CTG CAG TTA GCA TTT CGG CGC CTG AGC ATC ATT TAG for the N3A/N6D-mutation.

PCR reaction tubes containing: 0.5 µl template pGEM ZN23T [500 ng/µl], 5 pmol of each primer (Interactiva, Thermo Hybaid GmbH, Ulm, Germany), 5 µl of dNTP-mix ([10 mM], Applied Biosystems, CA, USA), 5 µl of PCR-buffer 10× (Applied Biosystems, CA, USA), 0.1 µl of AMPLITAQ™ DNA polymerase ([5 U/µl], Applied Biosystems, CA, USA) and sterile water to a final volume of 50 µl. The PCR-program consisted of 2 min at 94° C. followed by 30 cycles of 15 sec at 96° C., 15 sec at 50° C., 1 min at 72° C. and concluded with an additional min at 72° C. The PCR reactions were performed on GENEAMP® PCR System 9700 (Applied Biosystems, CA, USA).

The PCR-product was analysed on 1% agarose gel and, after confirming an obtained product of correct size, purified with QIAQUICK® PCR purification kit (QIAGEN GmbH, Hilden, Germany).

The PCR-products were cleaved according to Sambrook (Sambrook et al.) with the restriction enzymes AccI and PstI (New England Biolabs, NEB, MA, USA). The cleavage products were analysed on agarose gel and purified from the agarose with QIAQUICK® Gel Extraction Kit (QIAGEN GmbH, Hilden, Germany) prior to ligation. The fragments were ligated into a vector denoted "pTrp-protA-stab-(multi9)", already cleaved with the enzymes AccI and PstI and purified, by adding T4 DNA ligase and ligation buffer (MBI Fermentas, Lithuania), and subsequently transformed into RRIΔM15-cells (ATCC, MA, USA). The constructs were given the names pAY87 (Z(N23T/K4G)-Cys), pAY89 (Z(N23T/N3A)-Cys) and pAY91 (Z(N23T/N3A/N6D)-Cys), respectively.

A MEGABACE™ 1000 DNA Sequencing System (GE Healthcare, Uppsala, Sweden) was used to verify correct sequences of inserted fragments. MEGABACE™ terminator chemistry (GE Healthcare Uppsala, Sweden) was utilised according to the supplier's recommendations in a cycle sequencing protocol based on the dideoxy method (Sanger et al., 1977).

Example 4(b)

Non-Cysteine-Containing Monomer Construction

As template for the construction, a plasmid denoted "pTrp(-N)ZN23T-Cys", was used. This plasmid already contained the gene with the N23T-mutation.

A PCR-reaction was performed with this plasmid as template and the two oligonucleotides

AFFI-63:
TTT TTT GTA GAC AAC GGA TTC AAC AAA GAA C

-continued

GRTO-41:
GAT CTC GTC TAC TTT CGG CGC CTG AGC ATC ATT TAG for the K4G-mutation,

AFFI-64:
TTT TTT GTA GAC GCC AAA TTC AAC AAA GAA C

GRTO-41:
GAT CTC GTC TAC TTT CGG CGC CTG AGC ATC ATT TAG for the N3A-mutation,

AFFI-65:
TTT TTT GTA GAC AAC GGA TTC AAC AAA GAA C

GRTO-41:
GAT CTC GTC TAC TTT CGG CGC CTG AGC ATC ATT TAG and for the N3A/N6D-mutation.

PCR-reaction tubes containing: 0.5 μl template pTrp(-N)ZN23T-Cys [500 ng/μl], 5 pmol of each primer (Interactiva, Thermo Hybaid GmbH, Ulm, Germany), 5 μl of dNTP-mix (10 mM, Applied Biosystems, CA, USA), 5 μl of PCR-buffer 10× (Applied Biosystems, CA, USA), 0.1 μl of AMPLITAQ™ DNA polymerase ([5 UV], Applied Biosystems, CA, USA) and sterile water to a final volume of 504 The PCR-program consisted of 2 min at 94° C. followed by 30 cycles of 15 sec at 96° C., 15 sec at 50° C., 1 min at 72° C. and concluded with an additional min at 72° C. The PCR reactions were performed on GENEAMP® PCR System 9700 (Applied Biosystems, CA, USA).

The PCR-products were directly TA-cloned into the vector pGEM according to the manufacturer's instructions (Promega, Wis., USA) and subsequently transformed into RRIΔM15-cells (ATCC, MA, USA). The constructs were given the names pAY86 (Z(N23T/K4G), pAY88 (Z(N23T/N3A) and pAY90 (Z(N23T/N3A/N6D) respectively.

A MEGABACE™ 1000 DNA Sequencing System (GE Healthcare Uppsala, Sweden) was used to verify correct sequences of inserted fragments. MEGABACE™ terminator chemistry (GE Healthcare Uppsala, Sweden) was utilised according to the supplier's recommendations in a cycle sequencing protocol based on the dideoxy method (Sanger et al., 1977).

Example 5

Construction of the Gene Encoding Monomers and Oligomers with a C-Terminal Cysteine in pTrp-Vector All of the above described plasmids pAY 86 to pAY91 (a total of six plasmids) were cleaved with the restriction enzyme AccI. This resulted in releasing the Z-mutants completely from the pAY86-, pAY88- and pAY90-vectors and a single opening at the 3'-end of the gene in the pAY87-, pAY89- and pAY91-vectors.

The cleaved vectors were treated with Calf Intestine Alkaline Phosphatase (CIAP, MBI Fermentas, Lithuania) according to the manufacturer's recommendations. This step was performed to dephosphorylate the 5'-ends to avoid self-ligation of the vectors.

The released Z-mutant-fragments were analysed on agarose gel and subsequently purified from the agarose before the fragments was ligated into the opened vectors according to the following:

fragment from pAY86 to pAY87
fragment from pAY88 to pAY89
fragment from pAY90 to pAY91

For the ligation reactions, different proportions of fragment versus vector were mixed and the result was that a range of different multimers, as expected, ranging from dimers to pentamers was obtained.

The different multimers were transformed into RRIΔM15-cells (ATCC, MA, USA) and the correct sequences were verified by analysis on a sequencing equipment at the Royal Institute of Technology as described above. The newly constructed plasmids were denoted as shown in the table below:

TABLE 2

Summary of constructed plasmids

| Plasmid no. pAY | Expressed protein from construct |
|---|---|
| 86 | Z(N23T/K4G) |
| 87 | Z(N23T/K4G)-Cys |
| 88 | Z(N23T/N3A) |
| 89 | Z(N23T/N3A)-Cys |
| 90 | Z(N23T/N3A/N6D) |
| 91 | Z(N23T/N3A/N6D)-Cys |
| 92 | Z(N23T/K4G)dimer-Cys |
| 93 | Z(N23T/N3A)dimer-Cys |
| 94 | Z(N23T/N3A/N6D)dimer-Cys |
| 95 | Z(N23T/K4G)trimer-Cys |
| 96 | Z(N23T/N3A)trimer-Cys |
| 97 | Z(N23T/N3A/N6D)trimer-Cys |
| 98 | Z(N23T/K4G)tetramer-Cys |
| 99 | Z(N23T/N3A)tetramer-Cys |
| 100 | Z(N23T/N3A/N6D)tetramer-Cys |
| 101 | Z(N23T/K4G)pentamer-Cys |
| 102 | Z(N23T/N3A)pentamer-Cys |
| 103 | Z(N23T/N3A/N6D)pentamer-Cys |

The above described plasmid vectors, except pAY86, pAY88 and pAY90 have Trp promoter, Trp leader sequence and a gene for kanamycin (Km) resistance. pAY86, pAY88 and pAY90 have a gene for ampicillin resistance instead.

Example 6

Construction of Genes Encoding Monomers and Oligomers with a C-Terminal Cysteine in pK4-Vector The genes encoding the proteins as summarised in Table 2 were to be transferred to a vector containing SPA promoter and signal sequence. To enable this procedure, an adapter containing the cleavage site for the restriction enzyme KpnI (New England Biolabs, NEB, MA, USA) was to be constructed. The adapter was constructed by the two oligonucleotides (Interactiva, Thermo Hybaid GmbH, Ulm, Germany)

The plasmid pAY104 (pK4-cys-ABDstabdimer) was cleaved with FspI and PstI (New England Biolabs, NEB, MA, USA). The vector was purified on agarose gel and the released fragment was removed and the remaining vector was purified from the agarose with QIAQUICK® Gel Extraction Kit (QIAGEN GmbH, Hilden, Germany).

The two oligomers AFFI-88 and AFFI-89 were mixed in ligation buffer (MBI Fermentas, Lithuania) and heated to 50° C. and the mixture was allowed to cool to room temperature where after the cleaved plasmid vector was added together with T4 DNA ligase (MBI Fermentas, Lithuania). After the ligation reaction, the product was transformed into RRIΔM15-cells and the correct sequence was verified as described above. The resulting plasmid was denoted pAY128.

The plasmid pAY128 was then cleaved with the restriction enzymes KpnI and PstI and the cleaved vector was analysed on agarose gel and subsequently purified from the agarose with QIAQUICK® Gel Extraction Kit (QIAGEN GmbH, Hilden, Germany). The fragments expressing the two mutated Z-genes Z(N23T/N3A) and Z(N23T/N3A/N6A) from pAY86 to pAY103 were cleaved with KpnI and PstI (New England Biolabs, NEB, MA, USA), separated and purified after agarose gel separation. The different fragments were ligated into the cleaved vector originating from pAY128 and the resulting plasmids were, after verifying correct sequences, denoted pAY107 to pAY116 as summarised in Table 3.

TABLE 3

Summary of constructed plasmids with SPA promoter and signal sequence.

| Plasmid no. pAY | Expressed protein from construct |
|---|---|
| 107 | Z(N23T/N3A)-Cys |
| 108 | Z(N23T/N3A/N6D)-Cys |
| 109 | Z(N23T/N3A)dimer-Cys |
| 110 | Z(N23T/N3A/N6D)dimer-Cys |
| 111 | Z(N23T/N3A)trimer-Cys |
| 112 | Z(N23T/N3A/N6D)trimer-Cys |
| 113 | Z(N23T/N3A)tetramer-Cys |
| 114 | Z(N23T/N3A/N6D)tetramer-Cys |
| 115 | Z(N23T/N3A)pentamer-Cys |
| 116 | Z(N23T/N3A/N6D)pentamer-Cys |

Example 7

Construction of Genes Encoding a Part of the E-Gene (E') from Protein a N-Terminally Fused to Monomers and Oligomers with a C-Terminal Cysteine in pK4-Vector The genes encoding the proteins, as summarised in Table 2, were transferred to a vector containing the SPA promoter and signal sequence and a part of the gene encoding the E-region of protein A (E'). It has earlier been shown that an addition of the N-terminal IgG-binding part of the mature protein A (region E), or parts thereof, may increase correct processing and also facilitate secretion of the gene product to the surrounding culture medium (Abrahmsén et al., 1985). An adapter containing the cleavage site for the restriction enzyme KpnI and a part of region E from protein A (E') was constructed by the two oligonucleotides (Interactiva, Thermo Hybaid GmbH, Ulm, Germany)

The plasmid pAY104 (pK4-cys-ABDstabdimer) was cleaved with FspI and PstI (New England Biolabs, NEB, MA, USA). The vector was purified on agarose gel and the released fragment was removed and the remaining vector was purified from the agarose with QIAQUICK® Gel Extraction Kit (QIAGEN GmbH, Hilden, Germany). The two oligonucleotides were mixed in ligation buffer and heated to 75° C. and the mixture was allowed to cool to room temperature where after the cleaved plasmid vector was added, together with T4 DNA ligase (MBI Fermentas, Lithuania). After the ligation reaction the product was transformed into RRIΔM15-cells and the correct sequence was verified as described above. The resulting plasmid was denoted pAY129.

The plasmid pAY129 was then cleaved with the restriction enzymes KpnI and PstI and the cleaved vector was analysed on agarose gel and subsequently purified from the agarose with QIAQUICK® Gel Extraction Kit (QIAGEN GmbH, Hilden, Germany). The fragments expressing the two mutated Z-genes Z(N23T/N3A) and Z(N23T/N3A/N6A) from pAY86 to pAY103 were cleaved with KpnI and PstI, separated and purified after agarose gel separation. The different fragments were ligated into the cleaved vector originating from pAY129 and the resulting plasmids were, after verifying correct sequences, denoted pAY118 to pAY127 as summarised in Table 4.

TABLE 4

Summary of constructed plasmids with SPA promoter and signal sequence and a part of region E from protein A-E'.

| Plasmid no. pAY | Expressed protein from construct |
|---|---|
| 118 | E'-Z(N23T/N3A)-Cys |
| 119 | E'-Z(N23T/N3A/N6D)-Cys |
| 120 | E'-Z(N23T/N3A)dimer-Cys |
| 121 | E'-Z(N23T/N3A/N6D)dimer-Cys |
| 122 | E'-Z(N23T/N3A)trimer-Cys |
| 123 | E'-Z(N23T/N3A/N6D)trimer-Cys |
| 124 | E'-Z(N23T/N3A)tetramer-Cys |
| 125 | E'-Z(N23T/N3A/N6D)tetramer-Cys |
| 126 | E'-Z(N23T/N3A)pentamer-Cys |
| 127 | E'-Z(N23T/N3A/N6D)pentamer-Cys |

Example 8

Stability Towards Alkaline Conditions

To evaluate the stability of the proteins towards alkaline conditions, four different proteins were tested in an environment of high pH. The different proteins were Z(N23T)dimer-Cys, Z(N23T/K4G)dimer-Cys, Z(N23T/N3A)dimer-Cys and Z(N23T/N3A/N6D)dimer-Cys.

(Z(N23T)dimer-Cys), (Z(N23T/N3A)dimer-Cys), (Z(N23T/N3A/N6D)dimer-Cys) and (Z(N23T/K4G)dimer-Cys) were cultivated in fermenters. The harvested media were purified and coupled to HF Agarose (GE Healthcare, Uppsala, Sweden) using standard methods before the alkaline tests. The HF agarose-coupled proteins were denoted as follows

| Z(N23T)dimer-Cys | U631049 |
| Z(N23T/K4G)dimer-Cys | U631079 |
| Z(N23T/N3A)dimer-Cys | U631064 |
| Z(N23T/N3A/N6D)dimer-Cys | U631063 |

The matrices were packed in columns (HR 5/2, GE Healthcare, Uppsala, Sweden) to a final volume ranging from 0.1 to 0.3 ml. The purification equipment used was an ÄKTA™ Explorer 10 (GE Healthcare, Uppsala, Sweden) with a UV sample flow cell with a path length of 2 mm (GE Healthcare, Uppsala, Sweden).

The buffers used contained
Running buffer: 25 mM Tris-HCl, 1 mM EDTA, 200 mM NaCl, 0.05% TWEEN™ 20, 5 mM ammonium acetate, pH 8.0
Elution buffer: 0.2 M acetic acid (HAc), pH 3.1
Cleaning-In-Place (CIP) buffer: 0.5 M NaOH A typical chromatographic run cycle consisted of
Equilibrium of the column with running buffer
Sample application of 10 mg polyclonal human IgG (hIgG) at 0.2 ml/min
Extensive washing-out of unbound proteins
Elution at 1.0 ml/min with elution buffer
Re-equilibration with running buffer
Cleaning-In-Place (CIP) with CIP-buffer with a contact time between column matrix and 0.5 M NaOH of 1 hour
Re-equilibration with running buffer The amount of hIgG loaded at each run was well above the total dynamic binding capacity of the column since the breakthrough of unbound protein was considerable when loading the sample onto the columns in all cases.

After one cycle, including the steps above, a new cycle was started which again included one hour of exposure of 0.5 M sodium hydroxide. To measure the decrease of the dynamic binding capacity of the column the peak area of the eluted peak was compared with the original peak area of the eluted peak when the matrix had not been exposed to the sodium hydroxide. Setting the original peak area as 100% of binding capacity the decrease of the binding capacity of hIgG was observed. The peak area was calculated with the UNICORN™ software accompanying the purification system.

Figure 16:
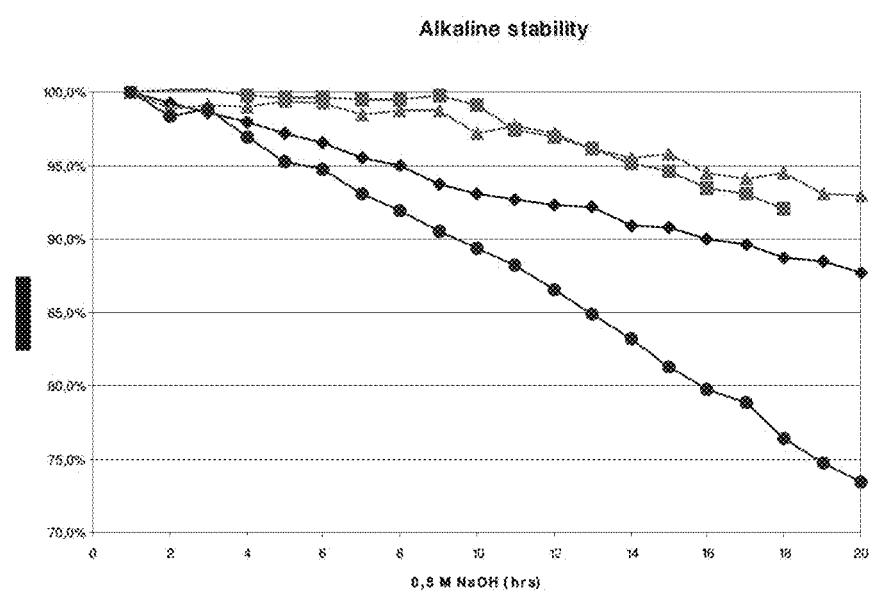
FIG. 16 shows graphs that represent the remaining dynamic binding capacity of the matrices in accordance with example 8. From top to bottom they represent Z(N23T/N3A/N6D)dimer-Cys, Z(N23T/N3A)dimer-Cys, Z(N23T)dimer-Cys and Z(N23T/K4G)dimer-Cys respectively. Due to software problems the last two measure points for Z(N23T/N3A)dimer-Cys are lacking.

Each cycle was repeated 21 times resulting in a total exposure time between the matrix and the sodium hydroxide of 20 hours for each different matrix. The normalised peak areas were visualised in a graph as can be seen below (FIG. 16). All 21 cycles were repeated for each mutant.

Both Z(N23T/N3A/N6D)dimer-Cys and Z(N23T/N3A) dimer-Cys showed improved stability against alkaline conditions compared to the originally produced Z(N23T)dimer-Cys.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A matrix for affinity chromatography, comprising a plurality of ligands coupled to a solid support, wherein the ligands comprise an immunoglobulin-binding protein, or multimer thereof, capable of binding to other regions of the immunoglobulin molecule than the complementarity determining regions (CDR), wherein at least the asparagine residue at position 6 or 11 of a parental immunoglobulin-binding protein defined by SEQ ID NO. 1 or 2 has been mutated to an amino acid other than glutamine, which mutation has conferred an increased chemical stability at alkaline pH-values compared to the parental molecule.

2. The matrix of claim 1, wherein the ligands have been coupled to the support by thioether bonding.

3. The matrix of claim 1, wherein the support is a natural polymer material.

4. The matrix of claim 1, wherein the support is a polysaccharide.

5. The matrix of claim 1, which selectively binds an immunoglobulin selected from the group consisting of IgG, IgA, and IgM.

6. The matrix of claim 5, which selectively binds an IgG immunoglobulin.

7. The matrix of claim 1, wherein the ligands exhibit an increased binding capacity, during two or more separations with intermittent alkaline cleaning, compared to the parental protein molecule.

8. The matrix of claim 7, wherein the cleaning is performed with NaOH and the concentration thereof is up to about 1 M.

9. The matrix of claim 8, wherein the cleaning is performed with NaOH and the concentration thereof is about 0.5 M.

10. The matrix of claim 1, wherein the protein is an Fc fragment-binding protein.

11. The matrix of claim 1, wherein the protein mutation(s) are selected from the group consisting of N6A; N11 S; N11 S and N23T; N6A and N23 T; and N3A, N6D, and N23 T; and wherein the parental molecule comprises the sequence defined by SEQ ID NO. 2.

12. The matrix of claim 1, wherein the asparagine residue in position 23 has been mutated.

13. The matrix of claim 12, wherein the asparagine residue in position 23 has been mutated to a threonine residue.

14. The matrix of claim 1, wherein the ligands include multimers comprising two or more repetitive units of the protein.

15. The matrix of claim 14, wherein the protein units of the multimers are linked by elements including up to about 15 amino acids.

16. The matrix of claim 14, wherein the multimers further comprise one or more of the E, D, A, B, and C domains of *Staphylococcus* protein A.

17. The matrix of claim 14, wherein the multimers are tetramers.

18. The matrix of claim 14, wherein each protein unit is the protein defined by SEQ ID NO. 2 and includes the mutation N23T.

* * * * *

SEQUENCE LISTING

```
<160> NUMBER OF SEQ ID NOS: 35

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
  1               5                  10                  15

Leu His Leu Pro Asn Leu Asn Glu Glu Gln Arg Asn Gly Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 2
<211> LENGTH: 58
<212> TYPE: PRT
<213> ORGANISM: Staphylococcus aureus
<220> FEATURE:
<221> NAME/KEY: MUTAGEN
<222> LOCATION: (29)

<400> SEQUENCE: 2

Val Asp Asn Lys Phe Asn Lys Glu Gln Gln Asn Ala Phe Tyr Glu Ile
  1               5                  10                  15

Leu His Leu Pro Asn Leu Asn Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 3
<211> LENGTH: 58
<212> TYPE: PRT
<213> ORGANISM: Staphylococcus aureus
<220> FEATURE:
<221> NAME/KEY: MUTAGEN
```

```
<222> LOCATION: (29)
<220> FEATURE:
<221> NAME/KEY: MUTAGEN
<222> LOCATION: (30)

<400> SEQUENCE: 3
```

Val Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Ala Ala Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

```
<210> SEQ ID NO 4
<211> LENGTH: 58
<212> TYPE: PRT
<213> ORGANISM: Staphylococcus aureus
<220> FEATURE:
<221> NAME/KEY: MUTAGEN
<222> LOCATION: (23)

<400> SEQUENCE: 4
```

Val Asp Asn Lys Phe Asn Lys Glu Gln Gln Asn Ala Phe Tyr Glu Ile
 1               5                  10                  15

Leu His Leu Pro Asn Leu Thr Glu Glu Gln Arg Asn Gly Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

```
<210> SEQ ID NO 5
<211> LENGTH: 33
<212> TYPE: PRT
<213> ORGANISM: Staphylococcus aureus

<400> SEQUENCE: 5
```

Ala Asn Asn Phe Asn Lys Glu Gln Asn Met Ala Phe Tyr Glu Ile Leu
 1               5                  10                  15

His Leu Pro Asn Leu Asn Glu Glu Ser Arg Asn Gly Glu Ser Gln Ser
             20                  25                  30

Leu

```
<210> SEQ ID NO 6
<211> LENGTH: 31
<212> TYPE: PRT
<213> ORGANISM: Staphylococcus aureus

<400> SEQUENCE: 6
```

Ala Asn Lys Phe Asn Lys Glu Gln Gln Asn Thr Phe Tyr Glu Ile Leu
 1               5                  10                  15

His Leu Pro Val Leu Lys Glu Ile Gln Arg Asn Gly Phe Ile Gln
             20                  25                  30

```
<210> SEQ ID NO 7
<211> LENGTH: 38
<212> TYPE: PRT
<213> ORGANISM: Staphylococcus aureus

<400> SEQUENCE: 7
```

```
Ala Ala Gln Gln Lys Asn Asn Asp Glu Ser Gln Asn Ala Asn Met Glu
1               5                   10                  15

Ile Leu His Leu Pro Asn Leu Asn Glu Glu Gln Arg Asn Gly Phe Ile
            20                  25                  30

Gln Ser Glu Ser Asp Ser
            35
```

<210> SEQ ID NO 8
<211> LENGTH: 38
<212> TYPE: PRT
<213> ORGANISM: Staphylococcus aureus

<400> SEQUENCE: 8

```
Ala Gln His Asp Glu Ala Glu Gln Gln Gln Val Phe Asn Met Ile Leu
1               5                   10                  15

His Ala Asp Asn Leu Asn Glu Glu Gln Arg Asn Gly Val Ile Gln Ser
            20                  25                  30

Gln Lys Asp Ser Pro Ser
            35
```

<210> SEQ ID NO 9
<211> LENGTH: 31
<212> TYPE: PRT
<213> ORGANISM: Staphylococcus aureus

<400> SEQUENCE: 9

```
Val Asp Asn Lys Phe Asn Lys Glu Gln Gln Asn Ala Phe Tyr Ala Ile
1               5                   10                  15

Leu His Leu Pro Asn Leu Asn Glu Glu Gln Arg Asn Gly Phe Ile
            20                  25                  30
```

<210> SEQ ID NO 10
<211> LENGTH: 72
<212> TYPE: PRT
<213> ORGANISM: Staphylococcus aureus

<400> SEQUENCE: 10

```
Met Lys Ala Ile Phe Val Leu Asn Ala Gln His Asp Glu Ala Val Asp
1               5                   10                  15

Asn Lys Phe Asn Lys Glu Gln Gln Asn Ala Phe Tyr Glu Ile Leu His
            20                  25                  30

Leu Pro Asn Leu Asn Glu Glu Gln Arg Asn Ala Phe Ile Gln Ser Leu
            35                  40                  45

Lys Asp Asp Pro Ser Gln Ser Ala Asn Leu Leu Glu Ala Lys Lys
    50                  55                  60

Leu Asn Asp Ala Gln Ala Pro Lys
 65                  70
```

<210> SEQ ID NO 11
<211> LENGTH: 36
<212> TYPE: PRT
<213> ORGANISM: Staphylococcus aureus

<400> SEQUENCE: 11

```
Gln Gln Asn Gly Thr Ala Leu His Leu Pro Asn Leu Asn Glu Glu Gln
1               5                   10                  15

Arg Asn Ala Phe Ile Gln Ser Leu Lys Asp Asp Pro Ser Gln Ser Ala
            20                  25                  30

Asn Leu Leu Ala
```

<210> SEQ ID NO 12
<211> LENGTH: 198
<212> TYPE: DNA
<213> ORGANISM: Artificial Sequence
<220> FEATURE:
<223> OTHER INFORMATION: Description of Artificial Sequence: synthetic
      DNA construct
<220> FEATURE:
<221> NAME/KEY: CDS
<222> LOCATION: (1)..(186)

<400> SEQUENCE: 12

```
ctg ggt acc gta gac gcc aaa ttc gac aaa gaa caa caa aac gcg ttc      48
Leu Gly Thr Val Asp Ala Lys Phe Asp Lys Glu Gln Gln Asn Ala Phe
 1               5                  10                  15 tat gag atc tta cat tta cct aac tta act gaa gaa caa cga aac gcc      96
Tyr Glu Ile Leu His Leu Pro Asn Leu Thr Glu Glu Gln Arg Asn Ala
             20                  25                  30 ttc atc caa agt tta aaa gat gac cca agc caa agc gct aac ctt tta     144
Phe Ile Gln Ser Leu Lys Asp Asp Pro Ser Gln Ser Ala Asn Leu Leu
         35                  40                  45 gca gaa gct aaa aag cta aat gat gct cag gcg ccg aaa tgc             186
Ala Glu Ala Lys Lys Leu Asn Asp Ala Gln Ala Pro Lys Cys
     50                  55                  60 taactgcagc tc                                                        198
```

<210> SEQ ID NO 13
<211> LENGTH: 62
<212> TYPE: PRT
<213> ORGANISM: Artificial Sequence
<220> FEATURE:
<223> OTHER INFORMATION: Description of Artificial Sequence: synthetic
      peptide encoded by DNA construct

<400> SEQUENCE: 13

```
Leu Gly Thr Val Asp Ala Lys Phe Asp Lys Glu Gln Gln Asn Ala Phe
 1               5                  10                  15

Tyr Glu Ile Leu His Leu Pro Asn Leu Thr Glu Glu Gln Arg Asn Ala
             20                  25                  30

Phe Ile Gln Ser Leu Lys Asp Asp Pro Ser Gln Ser Ala Asn Leu Leu
         35                  40                  45

Ala Glu Ala Lys Lys Leu Asn Asp Ala Gln Ala Pro Lys Cys
     50                  55                  60
```

<210> SEQ ID NO 14
<211> LENGTH: 192
<212> TYPE: DNA
<213> ORGANISM: Artificial Sequence
<220> FEATURE:
<223> OTHER INFORMATION: Description of Artificial Sequence: synthetic
      DNA construct
<220> FEATURE:
<221> NAME/KEY: CDS
<222> LOCATION: (1)..(180)

<400> SEQUENCE: 14

```
ttt ttt gta gac gcc aaa ttc gac aaa gaa caa caa aac gcg ttc tat      48
Phe Phe Val Asp Ala Lys Phe Asp Lys Glu Gln Gln Asn Ala Phe Tyr
 1               5                  10                  15 gag atc tta cat tta cct aac tta act gaa gaa caa cga aac gcc ttc      96
Glu Ile Leu His Leu Pro Asn Leu Thr Glu Glu Gln Arg Asn Ala Phe
             20                  25                  30
```

```
atc caa agt tta aaa gat gac cca agc caa agc gct aac ctt tta gca    144
Ile Gln Ser Leu Lys Asp Asp Pro Ser Gln Ser Ala Asn Leu Leu Ala
         35                  40                  45 gaa gct aaa aag cta aat gat gct cag gcg ccg aaa gtagacaaaa aa      192
Glu Ala Lys Lys Leu Asn Asp Ala Gln Ala Pro Lys
     50                  55                  60
```

<210> SEQ ID NO 15
<211> LENGTH: 60
<212> TYPE: PRT
<213> ORGANISM: Artificial Sequence
<220> FEATURE:
<223> OTHER INFORMATION: Description of Artificial Sequence: synthetic peptide encoded by DNA construct

<400> SEQUENCE: 15

Phe Phe Val Asp Ala Lys Phe Asp Lys Glu Gln Gln Asn Ala Phe Tyr
 1               5                  10                  15

Glu Ile Leu His Leu Pro Asn Leu Thr Glu Glu Gln Arg Asn Ala Phe
             20                  25                  30

Ile Gln Ser Leu Lys Asp Asp Pro Ser Gln Ser Ala Asn Leu Leu Ala
         35                  40                  45

Glu Ala Lys Lys Leu Asn Asp Ala Gln Ala Pro Lys
     50                  55                  60

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: synthetic DNA construct

<400> SEQUENCE: 16
gcagggtacc ctgca                                                    15

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: synthetic DNA construct

<400> SEQUENCE: 17
gggtaccctg c                                                        11

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: synthetic DNA construct

<400> SEQUENCE: 18
gcaaatgctg cgcagggtac cctgcagggg ggggggggaa                         40

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: synthetic DNA construct -continued

<400> SEQUENCE: 19
gcaacacgat gaagccggta ccctgca                                              27

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 20
gggtaccggc ttcatcgtgt tgc                                                  23

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 21
gcaaatgctg cgcaacacga tgaagccggt accctgcagg ggggggggg                      50

<210> SEQ ID NO 22
<211> LENGTH: 137
<212> TYPE: PRT
<213> ORGANISM: Artificial Sequence
<220> FEATURE:
<223> OTHER INFORMATION: Description of Artificial Sequence: synthetic
      peptide multimer

<400> SEQUENCE: 22

Val Asp Ala Lys Phe Asn Val Asp Asn Lys Phe Asn Lys Glu Gln
 1               5                  10                  15

Gln Asn Ala Phe Tyr Glu Ile Leu His Leu Pro Asn Leu Thr Glu
                20                  25                  30

Glu Gln Arg Asn Ala Phe Ile Gln Ser Leu Lys Asp Asp Pro Ser
                35                  40                  45

Gln Ser Ala Asn Leu Leu Ala Glu Ala Lys Lys Leu Asn Asp Ala
                50                  55                  60

Gln Ala Pro Lys Gln Ala Pro Lys Val Asp Ala Lys Phe Asn Val
                65                  70                  75

Asp Asn Lys Phe Asn Lys Glu Gln Gln Asn Ala Phe Tyr Glu Ile
                80                  85                  90

Leu His Leu Pro Asn Leu Thr Glu Glu Gln Arg Asn Ala Phe Ile
                95                 100                 105

Gln Ser Leu Lys Asp Asp Pro Ser Gln Ser Ala Asn Leu Leu Ala
               110                 115                 120

Glu Ala Lys Lys Leu Asn Asp Ala Gln Ala Pro Lys Gln Ala Pro
               125                 130                 135

Lys Cys

<210> SEQ ID NO 23
<211> LENGTH: 195
<212> TYPE: PRT
<213> ORGANISM: Artificial Sequence
<220> FEATURE:
<223> OTHER INFORMATION: Description of Artificial Sequence: synthetic
      peptide multimer

<400> SEQUENCE: 23

Val Asp Ala Lys Phe Asp Val Asp Asn Lys Phe Asn Lys Glu Gln
 1               5                  10                  15

Gln Asn Ala Phe Tyr Glu Ile Leu His Leu Pro Asn Leu Thr Glu
             20                  25                  30

Glu Gln Arg Asn Ala Phe Ile Gln Ser Leu Lys Asp Asp Pro Ser
         35                  40                  45

Gln Ser Ala Asn Leu Leu Ala Glu Ala Lys Lys Leu Asn Asp Ala
     50                  55                  60

Gln Ala Pro Lys Gln Ala Pro Lys Val Asp Ala Lys Phe Asp Val
 65                  70                  75

Asp Asn Lys Phe Asn Lys Glu Gln Gln Asn Ala Phe Tyr Glu Ile
             80                  85                  90

Leu His Leu Pro Asn Leu Thr Glu Glu Gln Arg Asn Ala Phe Ile
             95                 100                 105

Gln Ser Leu Lys Asp Asp Pro Ser Gln Ser Ala Asn Leu Leu Ala
         110                 115                 120

Glu Ala Lys Lys Leu Asn Asp Ala Gln Ala Pro Lys Val Asp Asn
     125                 130                 135

Lys Phe Asn Lys Glu Gln Gln Asn Ala Phe Tyr Glu Ile Leu His
             140                 145                 150

Leu Pro Asn Leu Asn Glu Glu Gln Arg Asn Ala Phe Ile Gln Ser
             155                 160                 165

Leu Lys Asp Asp Pro Ser Gln Ser Ala Asn Leu Leu Ala Glu Ala
         170                 175                 180

Lys Lys Leu Asn Asp Ala Gln Ala Pro Lys Gln Ala Pro Lys Cys
     185                 190                 195

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24 tttttgtag acaacggatt caacaaagaa c                              31

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
gatctgctgc agttagcatt tcggcgcctg agcatcattt ag                 42

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 26 tttttgtag acgccaaatt caacaaagaa c                              31

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 27
gatctgctgc agttagcatt tcggcgcctg agcatcattt ag                           42

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28 tttttgtag acgccaaatt cgacaaagaa c                                        31

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 29
gatctgctgc agttagcatt tcggcgcctg agcatcattt ag                           42

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 30 tttttgtag acaacggatt caacaaagaa c                                        31

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 31
gatctcgtct actttcggcg cctgagcatc atttag                                  36

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 32 tttttgtag acgccaaatt caacaaagaa c                                        31

```
<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 33
gatctcgtct actttcggcg cctgagcatc atttag                                36

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 34 tttttttgtag acaacggatt caacaaagaa c                                    31

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 35
gatctcgtct actttcggcg cctgagcatc atttag                                36
```